United States Patent
Su

(10) Patent No.: US 7,247,443 B2
(45) Date of Patent: Jul. 24, 2007

(54) SENSOR CONSTRUCTS AND DETECTION METHODS

(75) Inventor: Wei-Wen Su, Honolulu, HI (US)

(73) Assignee: University of Hawaii, Honolulu, HI (US)

(*) Notice: Subject to any disclaimer, the term of this patent is extended or adjusted under 35 U.S.C. 154(b) by 0 days.

(21) Appl. No.: 11/083,461

(22) Filed: Mar. 17, 2005

(65) Prior Publication Data

US 2006/0068502 A1 Mar. 30, 2006

Related U.S. Application Data

(60) Provisional application No. 60/554,313, filed on Mar. 17, 2004.

(51) Int. Cl.

| | |
|---|---|
| *G01J 3/30* | (2006.01) |
| *G01J 1/58* | (2006.01) |
| *G01N 21/25* | (2006.01) |
| *G01N 21/64* | (2006.01) |
| *G01N 33/53* | (2006.01) |
| *G01N 21/00* | (2006.01) |
| *G01N 21/75* | (2006.01) |
| *G01N 21/76* | (2006.01) |
| *C07K 1/00* | (2006.01) |
| *F21V 9/16* | (2006.01) |
| *C12Q 1/68* | (2006.01) |

(52) U.S. Cl. .............. 435/7.1; 356/317; 356/318; 356/417; 250/458.1; 250/459.1; 250/461.1; 250/461.2; 435/6; 436/164; 436/166; 436/172; 530/350

(58) Field of Classification Search ............. 356/317, 356/318, 417; 250/458.1, 459.1, 461.1, 461.2; 435/6, 7.1; 436/164, 166, 172; 530/350
See application file for complete search history.

(56) References Cited

U.S. PATENT DOCUMENTS

| | | | |
|---|---|---|---|
| 5,945,526 A | 8/1999 | Lee et al. | 536/26.6 |
| 5,998,204 A | 12/1999 | Tsien et al. | 435/325 |
| 6,147,203 A * | 11/2000 | Pastan et al. | 536/23.53 |
| 6,197,928 B1 | 3/2001 | Tsien et al. | 530/350 |

(Continued)

FOREIGN PATENT DOCUMENTS

WO  WO 03/025220 A2  3/2003

OTHER PUBLICATIONS

Joelle N. Pelletier, Katja M. Arndt, Andreas Pluckthun, and Stephen W. Michnick; An in vivo library-versus-library selection of optimized protein—protein interactions. Nature Biotechnology. vol. 17, Jul. 1999: 683-690.*

(Continued)

*Primary Examiner*—Long V. Le
*Assistant Examiner*—Jacqueline A. DiRamio
(74) *Attorney, Agent, or Firm*—Michael Fedrick; Sheldon Mak Rose & Anderson PC

(57) ABSTRACT

Sensor constructs for detecting the presence of an analyte in a sample comprise a molecular scaffold, a pair of labels which interact via Förster resonance energy transfer, and at least one molecular recognition domain. When the analyte is bound by the molecular recognition domain, the Förster resonance energy interaction between the pair of labels is disrupted, resulting in a changed optical signal.

34 Claims, 10 Drawing Sheets

U.S. PATENT DOCUMENTS

| | | | |
|---|---|---|---|
| 6,593,091 B2* | 7/2003 | Keys et al. ............... | 435/6 |
| 6,600,014 B2* | 7/2003 | Ogino et al. ............... | 530/324 |
| 6,670,159 B1* | 12/2003 | Savage et al. ............. | 435/192 |
| 2003/0084311 A1* | 5/2003 | Wolf ........................ | 435/7.1 |

OTHER PUBLICATIONS

Lubert Stryer; Richard P. Haugland; *Energy Transfer: A Spectroscopic Ruler;* Proc. N.A.S., vol. 58, 1967, pp. 719-726.

Cheryl A. Guyer; David G. Morgan; James V. Staros, *Binding Specificity of the Periplasmic Oligopeptide-Binding Protein from Escherichia coli,* Journal of Bacteriology, Nov. 1986, vol. 168, No. 2, pp. 775-779.

James J. Devlin; Lucy C. Panganiban; Patricia E. Devlin, *Random Peptide Libraries: A Source of Specific Protein Binding Molecules,* Science, New Series, vol. 249, No. 4967 (Jul. 27, 1990), pp. 404-406.

Philip E. Dawson; Tom W. Muir; Ian Clark-Lewis; Stephen B.H. Kent, *Synthesis of Proteins by Native Chemical Ligation,* Science, New Series, vol. 266, No. 5186 (Nov. 4, 1994), pp. 776-779.

Valerie A. Romoser, Patricia M. Hinkle; Anthony Persechini, *Detection in Living Cells of Ca 2+-dependent Changes in the Fluorescence Emission of an Indicator Composed of Two Green Fluorescent Protein Variants Linked by a Calmodulin-binding Sequence,* The Journal of Biological Chemistry, vol. 272, No. 20, Issue of May 16, pp. 13270-13274, 1997.

Miyawaki A.; Llopis J.; Heim R.; McCarffery J.M.; Adams J.A.; Ikura M.; Tsien R. Y., *Fluorescent indicators for Ca2+ based on green fluorescent proteins and calmodulin,* Nature Aug. 28, 1997; 388 (6645): 882-7, -abstract only.

Douglas C. Youvan; Christopher M. Silva; Edward J. Bylina; William J. Coleman; Michael R. Dilworth; Mary M. Yang, *Calibration of Fluorescence Resonance Energy Transfer in Microscopy Using Genetically Engineered GFP Derivatives on Nickel Chelating Beads,* Biotechnology et alia, 1997 3: pp. 1-18.

Gerald W. Gordon; Gail Berry; Xiao Huan Liang; Beth Levine; Brian Herman, *Quantitative Fluorescence Resonsance Energy Transfer Measurements Using Fluorescence Microscopy,* Biophysical Jouranl vol. 74, May 1998, pp. 2702-2713.

Worn A.; Pluckthun A., *Mutual stabilization of VL and VH in single-chain antibody fragments, investigated with mutants enginnered for stability,* Biochemistry Sep. 22, 1998; 37 (38): 13120-7, -abstract only.

Yao Xu; David Piston; Carl Hirschie Johnson, *A bioluminescence resonsance energy transfer (BRET) system: Application to interacting circadian clock proteins,* Proc. Natl. Acad. Sci. vol. 96, pp. 151-156, Jan. 1999.

Brian A. Pollok; Roger Heim, *Using GFP in FRET-based applications,* Cell Biology (vol. 9) Feb. 1999, pp. 57-60.

Atsushi Miyawaki; Oliver Griesbeck; Roger Heim; Roger Y. Tsien, *Dynamic and quantitative Ca2+ measurements using improved cameleons,* Proc. Natl;. Acad. Sci. vol. 96, pp. 2135-2140, Mar. 1999.

Fusheng Li; Shan-Lu Liu; James I. Mullins, *Homogeneous Noncompetitive Immunoassay based on the energy transfer between fluor-olabeled antibody variable domains (open sandwich fluoroimmunoassay),* BioTechniques 27: 738-742 (Oct. 1999).

Gethyn J. Allen; June M. Kwak; Sarah P. Chu; Juan Llopis; Roger Y. Tsien; Jeffrey F. Harper and Julian I. Schroeder, *Cameleon calcium indicator reports cytoplasmic calcium dynamics in Arabidopsis guard cells,* The Plant Journal (1999) 19(6), 735-747.

Chikako Suzuki; Hiroshi Ueda; Kouhei Tsumoto; Walt C. Mahoney; Izumi Kumagai; Teruyuki Nagamune, *Open sandwich ELISA with VH-/VI-alkaline phospatase fusion,* Journal of Immunological Methods 224 (1999) 171-184.

Ueda H.; Kubota K.; Wang Y.; Tsumoto K.; Mahoney W.; Kumagai I.; Nagamune T., *Homogeneous noncompetitive immunoassay based on the energy transfer between fluorolabeled antibody variable domains (open sandwich fluoroimmunoassay),* Biotechniques Oct. 27, 1999(4): 738-42, -abstract only.

Zaccolo M.; De Glorgi F.; Cho C.Y.; Feng L.; Knapp T.; Negulescu P.A.; Taylor S.S.; Tsien R.Y.; Pozzan T., *A genetically encoded, fluorescent indicator for cyclic AMP in living cells,* Nat Cell Biol. Jan. 2000:2(1): 25-9, -abstract only.

David P. Meininger; Mark Rance; Melissa A. Starovasnik; Wayne J. Fairbrother; Nicholas J. Skelton, *Characterization of the binding interface between the E-Domain of Staphylococcal protein A and an antibody Fv-Fragment,* Biochemistry 2000, 39, 26-36.

Paul R. Selvin, *The renaissance of fluorescence resonance energy transfer,* Nature Structural Biology, vol. 7, No. 9, Sep. 2000.

Ching-Hsuan Tung, *Preparation and applications of peptide-oligonucleotide conjugates,* Bioconjugate Chemistry, vol. 11, No. 5, Sep./Oct. 2000.

Katja M. Arndt; Joelle N. Pelletier; Kristian M. Muller; Tom Alber; Stephen W. Michnick; Andreas Pluckthun, *A heterodimeric coiled-coil peptide pair selected in vivo from a designed libray-versus-library ensemble,* J. Mol. Biol. (2000) 295, 627-639.

Akira Honda; Stephen R. Adams; Carolyn L. Sawyer; Varda Lev-Ram; Roger Y. Tsien; Wolfgang R. G. Dostmann, *Spatiotemporal dynamics of guanosine 3', 5'-cyclic monophosphate revealed by a genetically encoded, fluorescent indicator,* PNAS, Feb. 27, 2001, vol. 98, No. 5, pp. 2437-2442.

Katja M. Arndt; Kristian M. Muller; Andreas Pluckthun, *Helix-stabilized Fv (hsFv) antibody fragments; substituting the constant domains of a fab fragment for a heterodimeric coiled-coil domain,* J. Mol. Biol. (2001) 312, 221-228.

Minnie M. Wu; Michael Grabe; Stephen Adams; Roger Y. Tsien; Hsiao-Ping H. Moore; Terry E. Machen, *Mechanisms of pH regulation in the regulated secretory pathway,* The Journal of Biological Chemistry, vol. 276, No. 35, Issue of Aug. 31, pp. 33027-33035, 2001.

Alice Y. Ting; Kristin H. Kain; Richard L. Klemke; Roger Y. Tsien, *Genetically encoded fluorescent reporters of protein tyrosine kinase activities in living cells,* PNAS Dec. 18, 2001 vol. 98, No. 26 pp. 15003-15008.

Robert M. De Lorimier; J. Jeff Smith Mary A. Dwyer; Loren L. Looger; Kevin M. Sali; Chad D. Paavola; Shahir S. Rizk; Shamil Sadigov; David W. Conrad; Leslie Loew; Homme W. Hellinga, *Construction of a fluorescent biosensor family,* Protein Science (2002), 11: 2655-2675.

Mark Stitt, *Imaging of metabolites by using a fusion protein between a periplasmic binding protein and GFP derivatives: From a chimera to a view of reality,* PNAS, Jul. 23, 2002, vol. 99, No. 15 pp. 9614-9616.

Marcus Fehr; Wolf B. Frommer; Sylvie Lalonde, *Visualization of maltose uptake in living yeast cells by fluorescent nanosensors,* PNAS, Jul. 23, 2002, vol. 99, No. 15, pp. 9846-9851.

Jennifer R. Litowski; Robert S. Hodges, *Designing Heterodimeric Two-stranded -Helical coiled-coils,* The Journal of Biological Chemistry, vol. 277, No. 40, Issue of Oct. 4, pp. 37272-37279, 2002.

Yoshiyuki Ohiro; Ryoichi Arai; Hiroshi Ueda; Teruyuki Nagamune, *A homogeneous and noncompetitive immunoassay based on the enhanced fluorescence resonance energy transfer by leucine zipper interaction,* Anal. Chem. 2002, 74, 5786-5792.

Jin Zhang; Robert E. Campbell; Alice Y. Ting; Roger Y. Tsien, *Creating new fluorescent probes for cell biology,* Nature Reviews, Molecular Cell Biology, vol. 3, Dec. 2002, pp. 906-918.

R.H. Meloen; W.C. Puijk; J.P.M. Langeveld; J.P.M. Langedijk; P. Timmerman, *Design of synthetic peptides for diagnostics,* Current Protein and Peptide Science, 2003, 4, 253-260.

Yuling Yan; Gerard Marriott, *Analysis of protein interactions using fluorescence technologies,* Current Opinion in Chemical Biology 2003, 7:635-640.

Darcy J. Lichlyter; Sheila A. Grant; Orhan Soykan, *Develoment of a novel FRET immunosensor technique,* Biosensors and Bioelectronics 19 (2003) 219-226.

Courtenay Hart; Birte Schulenberg; Zhenjun Diwu; Wai-Yee Leung; Wayne F. Patton, *Fluorescence detection and quantitation of recombinant proteins containing oligohistidine tag sequences directly in sodium dodecyl sulfate-polyacrylamide gels,* Electrophoresis 2003, 24, 599-610.

Ida Lager; Marcus Fehr; Wolf B. Frommer; Sylvie Lalonde, *Development of a fluorescent nanosensor for ribose*, FEBS Letters 553 (2003) 85-89.

Marcus Fehr; Sylvie Lalonde; Ida Lager; Michael W. Wolff; Wolf B. Frommer, *In vivo imaging of the dynamics of glucose uptake in the cytosol of cos-7 cells by fluorescent nanosensors*, The Journal of Biological Chemistry, vol. 278, No. 21, Issue of May 23, pp. 19127-19133, 2003.

Igor L. Medintz; Aaron R. Clapp; Hedi Mattoussi; Ellen R. Goldman; Brent Fisher; J. Matthew Mauro, *Self-assembled nanoscale biosensors based on quantum dot FRET donors*, Nature materials vol. 2, Sep. 2003, pp. 630-638.

Darcy J. Lichlyter; Sheila A. Grant; Orhan Soykan, *Development of a novel FRET immunosensor technique*, Biosensors and Bioelectronics, vol. 19, Issue 3, Nov. 30, 2003, pp. 219-226, -abstract only.

Tsutomu Tanaka; Noriho Kamiya; Teruyuki Nagamune, *Peptidyl linkers for protein heterodimerization catalyzed by microbial transglutaminase*, Bioconjugate Chem. 2004, 15, 491-497.

Ian E. Gentle; David P. De Souza; Manuel Baca, *Direct production of proteins with N-Terminal Cystein for Site-Specific Conjugation*, Bioconjugate Chem. 2004, 15, 658-663.

H. Li; L. Ying; X. Ren; S. Blasubramanian; D. Klenerman, *Fluorescence studies of single biomolecules*, Biochemical Society Transactions (2204) vol. 32, Part 5.

Henrik G. Svensson; William J. Wedemeyer; Jennifer L. Ekstrom; David R. Callender; Tanja Kortemme; David E. Kim; Ulf Sjobring; David Baker, *Contributions of amino acid side chains to the kinetics and thermodynamics of the bivalent binding of protein L. to Ig k light chain*, Biochemistry 2004, 43, 2445-2457.

Rosanto I. Paramban; Robert C. Bugos; Wei Wen Su, *Engineering green fluorescent protein as a dual functional tag*, Biotechnology and Bioengineering, vol. 86, No. 6, Jun. 20, 2004.

Fehr M.; Okumoto S.; Deuschle K.; Lager I.; Looger L.L.; Persson J.; Kozhukh L.; Lalonde S.; Frommer W.B., *Development and use of fluorescent nanosensors for metabolite imaging in living cells*, Biochem Soc. Trans. Feb. 2005; 33 (pt 1): 287-90, -abstract only.

Ville Laitala; Ilkka Hemmila, *Homogeneous assay based on antistokes' shift time-resolved fluorescence resonance energy-transfer measurement*, Analytical Chemistry, vol. 77, No. 5, Mar. 1, 2005, pp. 1483-1487.

Loren L. Looger; Sylvie Lalonde; Wolf B. Frommer, *Genetically encoded FRET sensors for visualizing metabolites with subcellular resolution in living cells*, Plant Physiology, Jun. 2005, vol. 138, pp. 555-557.

James N. Miller, Fluorescence energy transfer methods in bioanalysis, Analyst, 2005, 130, 265-270.

Roger Y. Tsien, *Building and breeding molecules to spy on cells and tumors*, FEBS Letters 579 (2005) 927-932.

Angelika Ziegler; Lesley Torrance; Applications of recombinant antibodies in plant pathology, Molecular Plant Pathology (2002) 3(5), 401-407.

Rick Wiese; Yuri Belosludtsev; Tom Powdrill; Patricia Thompson; Mike Hogan, Simultaneous Multinanalyte ELISA Performed on a Microarray Platform, Clinical Chemistry 47: 8 1451-1457 (2001).

Selma Voss; Arne Skerra, Mutagenesis of a flexible loop in streptavidin leads to higher affinity for the Strep-tag II peptide and improved performance in recombinant protein purification, Protein Engineering vol. 10, No. 8, pp. 975-982, 1997.

K. Uhde; R.J. Kerschbaumer; R. Ooenig; S. Hirschl; O. Lemaire; N. Boonham; W. Roake; G. Himmler, Improved detection of beet necrotic yellow vein virus in a DAS ELISA by means of antibody single chain fragments (scFv) whcih were selected to proteasestable epitopes from phage display libraries, Arch. Virol (2000) 145: 179-185.

Sanjay Tyagi; Diana P. Bratu; Fred Russell Kramer, Multicolor molecular beacons for allele discrimination, Nature Biotechnology vol. 16 Jan. 1998.

Masumi Taki; Maki Shiota; Kazunari Taira, Transgulatminasemediated N- and C-terminal fluorescein labeling of a protein can support the native activity of the modified protein, Protein Engineering, Design & Selection vol. 17, No. 2, pp. 119-126, 2004.

Barry Schweitzer; Steven Wiltshire; Jeremy Lambert; Shawn O'Malley; Kari Kukanskis; Zhengrong Zhu; Stephen F. Kingsmore; Paul M. Lizardi; David C. Ward, Immunoassays with rolling circle DNa amplification: A versatile platform for ultrasensitive antigen detection, PNAS, Aug. 29, 2000, vol. 97, No. 18, pp. 10113-10119.

Gavin D. Meredith; Hayley Y. Wu; Nancy L. Allbritton, Targeted Protein Functionalization Using His-Tags, Bioconjugate Chem. 2004, 15, 969-982.

Maria M. Lopez; Edson Bertolini; Antonio Olmos; Paola Caruso; Maria Teresa Gorris; Pablo Llop; Ramon Penyalver; Mariano Cambra, Innovative tools for detection of plant pathogenic viruses and bacteria, Int Microbiol (2003) 6: 233-243.

Nicholas G. Housden; Steven Harrison; Hazel R. Housden; Karen-Anne Thomas; Jennifer A. Beckingham; Sian E. Roberts; Stephen P. Bottomly; Marc Graille; Enrico Stura; Michael G. Gore, Observation and characterization of the interaction between a single immunoglobulin binding domain of protein L and two equivalents of human k light chains, The Journal of Biological Chemistry, vol. 279, No. 10, Issue of Mar. 5, pp. 9370-9378, 2004.

B. Albert Griffin; Stephen R. Adams; Jay Jones; Robert Y. Tsien [40] Fluorescent labeling of recombinant proteins in living cells with FlAsH, Methods in Enzymology, vol. 327, pp. 565-578.

Rosella Franconi; Piero Roggero; Paola Pirazzi; Francisco Javier Arias; Angiola Desiderio; Orsola Bitti; Dimitre Pashkoulov; Benedetta Mattei; Luisa Bracci; Vera Masenga; Robert Geoffrey Milne; Eugenio Benvenuto, *Functional expression in bacteria and plants of scFv antiboy fragment against tospovirusses*, Immunotechnology 4 (1999) 189-201.

Arkady F. Fradkov; Ying Chen; Li Ding; Ekaterina V. Barsova; Mikhail V. Matz; Sergey A. Lukyanov, *Novel fluorescent protein from Discosoma coral and its mutants possesses a unique far-red fluorescence*, FEBS letters 479 (2000) 127-130.

Jeremy P. Derrick; Dale B. Wigley, *The third IgG-binding domain from streptococcal protein G*, J. Mol. Biol. (1994) 243,906-918.

Chiquito J. Crasto; Jin-an Feng, *Linker: a program to generate linker sequences for fusion proteins*, Protein Engineering, vol. 13, No. 5, pp. 309-312, 2000.

Anne M. Alvarez, *Intergrated approaches for detection of plant pathogenic bacteria and diagnosis of bacterial diseases*, Ann. Rev. Phytopathol, 2004, 42:339-66.

C.S. Yun; A. Javier; T. Jennings; M. Fisher; S. Hira; S. Peterson; B. Hopkins; N.O. Reich; G.F. Strouse, *Nanometal surface energy transfer in optical rulers, breaking the FRET barrier*, J. Am. Chem. Soc. 2005, 127, 3115-1229.

Karsten Winkler; Achim Kramer; Gabriele Juttner; Martina Seifert; Christa Scholz; Helga Wessner; Jens Schneider-Mergener; Wolfgang Hohne, *Changing the antigen binding specificity by single point mutations of an anti-p24 (HIV-1) antibody*, The Journal of Immunology, 2000, 165: 4505-4514.

Lubert Stryer, *Fluorescence energy transfer as a spectroscopic ruler*, Annu. Rev. Biochem. 1978: 47 819-846.

F.A. Saul; B. Vulliez-le Normand; F. Lema; G.A. Bentley, *Crystal structure of a recombinant form of the maltodextrin-binding protein carrying an inserted sequence of a B-cell epitope from the preS2 region of hepatitis B virus*, Proteins: Structure, Functins, and Genetics 27: 1-8 (1997).

Celine Monnet; Daniel Laune; Jeanny Laroche-Traineau; Martine Biard-Piechaczyk; Laurence Brain; Cedric Bes; Martine Pugniere; Jean-Claude Mani; Bernard Pau; Martine Cerutti; Gerard Devauchelle; Christian Devaux; Claude Granier; Thierry Chardes, *Synthetic peptides derived from the variable regions of an anti-CD4 monoclonal antibody bind to CD4 and inhibit HIV-1 promoter activation in virus-infected cells*, The Journal of Biological chemistry, vol. 274, No. 6, Issue of Feb. 5, pp. 3789-3796, 1999.

Pierre Martineau; Claude Leclerc; Maurice Hofnung, *Modulating the immunological properties of a linear B-cell epitope by insertion into permissive sites of the MalE Protein*, Molecular Immunology, vol. 33, No. 17/18, pp. 1345-1358, 1996.

Anne Lecroisey; Pierre Martineau; Maurice Hofnung; Muriel Delepierre, *NMR studies on the flexibility of the poliovirus C3 linear epitope inserted into different sites of the maltose-binding protein*, The Journal of Biological Chemistry, vol. 272, No. 1, Issue of Jan. 3, pp. 362-368 1997.

Markus Kaufmann; Peter Lindner; Annemarie Honegger; Kerstin Blank; Markus G. Grutter, *Crystal structure of the anti-His tag ntibody 3D5 single-chain frament complexed to its antigen,* J. Mol. Biol. (2002) 318, 135-147.

Achillefs N. Kapanidis; Yong W. Ebright; Richard H. Ebright, *Site-specific incorporation of fluorescent probes into protein: hexahistidine-tag-mediated fluorescent labeling with (Ni2+:Nitrilotriacetic acid)n-fluorochrome conjugates,* J. Am. Chem. Soc. 2001, 123, 12123-12125.

Milenen Hernandez; Ileana Rodriguez; Lilliam Pozo; Juan Rivero, *Chimeric synthetic peptides from the nucleocapsid p24 protein of human immunodeficiency virus type-1,* Biochemical and Biophysical Research Communications 282, 1-3 (2001).

Gurkan Guntas; Marc Ostermeier, *Creation of an allosteric enzyme by domain insertion,* J. Mol. Biol. (2004) 336, 263-273.

Sandrine Falipou; Jean-Marc Chovelon; Claude Martelet; Jacqueline Margonari; Dominique Cathignol, *New use of cyanosilane coupling agent for direct binding of antibodies to silica supports > Physicochemical characterization of molecularly bioengineered layers,* Bioconjugate Chem. 1999, 10, 346-353.

Nobuhide Doi; Hiroshi Yanagawa, *Design of generic biosensors based on green fluorescent proteins with allosteric sites by directed evolution,* FEBS Letters 453 (1999) 305-307.

Hans J. W. deHaard; Bert Kazemier; Marck J. M. Koolen; Liekle J. Nijholt; Rob H. Meloen; Bob van Gemen; Hennie R. Hoogenboom; Jan-Willem Arends, *Selection of recombinant, library-derived antibody fragments against p24 for human immunodeficiency virus type 1 diagnostics,* Clinical and Diagnostic Laboratory Immunology, Sep. 1998, p. 636-644.

Jean-Michel Betton; Pierre Martineau; William Saurin; Maurice Hofnung, *Location of tolerated insertions/deletions in the structure of the maltose binding protein,* FEBS 12372, vol. 325, No. 1, 2, 34-38, Jun. 1993.

Antoni Benito; Marc H.V. Van Regenmortel, *Biosensor characterization of antigenic site A of foot-and-mouth disease virus presented in different vector systems,* FEMS Immunology and Medical Microbiology 21 (1998) 101-115.

B. Albert Griffin; Stephen R. Adams; Robert Y. Tsien, Specific covalent labeling of recombinant protein molecules inside live cells, Science, vol. 281, Jul. 10, 1998, pp. 269-272.

B. Albert Griffin; Stephen R. Adams; Jan Jones; Robert Y. Tsien, [40] Fluorescent labling of recombinant proteins in living cells with FlAsH, Methods in Enzymology, vol. 327, pp. 565-578, Jul. 10, 1998.

\* cited by examiner

SENSOR CONSTRUCTS AND DETECTION METHODS

The present application claims priority from U.S. Provisional Patent Application No. 60/554,313, filed Mar. 17, 2004, entitled "Novel Fluorescent Nanosensor Proteins," the entire disclosure of which is hereby incorporated by reference.

BACKGROUND

Immunoassays and assays based on the polymerase chain reaction (PCR) are among the most widely used techniques for detecting analytes. While PCR-based techniques generally give good detection sensitivity, they have not been widely adopted for routine screening in many laboratories. One reason is that when PCR is used for detecting analytes in biological materials, its accuracy is strongly influenced not only by the performance of the PCR assay itself, but also by the quality of the nucleic acids extracted from the biological materials being tested. In addition, the detection sensitivity of PCR-based methods can be reduced by inhibitors in the extract that may interfere with the amplification process. Trained lab personnel are also required to conduct PCR assays in order to assure their accuracy.

Immunoassays are generally less expensive and require less training to perform. They have been adopted in a variety of formats, with enzyme linked immunosorbent assays (ELISAs), lateral-flow immunoassays, and Western-blot assays being the most common. Current ELISA and Western-blot techniques, however, require multiple incubation steps and are prone to operator error. Lateral-flow immunoassays are generally faster but are not as accurate as conventional ELISAs.

An alternative assay format has been proposed by Tsien, et al. for detecting analytes. This technique, described in U.S. Pat. No. 5,998,204, makes use of a protein having an analyte-binding region and two fluorescent labels. When the analyte-binding region binds an analyte, a conformational change occurs which causes the two fluorescent labels to change position relative to each other. This alters a fluorescence resonance energy interaction between the labels, which is detected in order to determine analyte binding.

Frommer, et al. have proposed a similar assay format in PCT International Application No. 03/025220. This assay makes use of a fusion protein that includes a periplasmic binding protein portion and two fluorescent protein portions. The fusion protein changes conformation upon binding an analyte, changing the relative positions of the two fluorescent protein portions. An altered fluorescence resonance energy interaction is thereby induced between the fluorescent protein moieties.

The assay systems disclosed by Tsien and Frommer both require the use of sensor constructs which change conformation upon binding an analyte of interest. Both, moreover, detect only small analytes such as simple sugars and amino acids. There remains a need, therefore, for a more general approach to analyte detection which takes advantage of resonance energy transfer interactions but which is not limited to constructs that must change conformation in order to detect an analyte or that detect only small analytes.

SUMMARY

The present method of detecting an analyte in a sample involves the use of a sensor construct that comprises: (i) a molecular recognition domain which specifically binds the analyte; (ii) a first label comprising an RET donor; and (iii) a second label comprising an RET acceptor for the RET donor. The RET acceptor is separated from the RET donor by a distance that allows Förster resonance energy transfer from the donor to the acceptor to occur, preferably by a distance of from about 1 to about 25 nanometers. When the molecular recognition domain of the sensor construct binds the analyte, proximity of the analyte to the RET donor and/or the RET acceptor interferes with a FRET interaction between the RET donor and RET acceptor, resulting in a detectable optical signal. The presence of the analyte in the sample is indicated by the detection of this optical signal.

The present methods can further include the more specific steps of measuring a control optical signal generated by a Förster resonance energy transfer interaction between the RET donor and the RET acceptor of the sensor construct prior to contacting the sensor construct with the sample, and then determining the difference between the control optical signal and the optical signal detected after contacting the sensor construct with the sample. The difference between this signal and the control optical signal is indicative of the amount of the analyte in the sample, thereby allowing quantitative detection of the analyte. Preferably, a change in the intensity or decay kinetics of the fluorescence or luminescence of the sensor construct is measured as the optical signal.

In the present methods, the RET donor can be any of a number of fluorescent or luminescent moieties, such as a fluorescent protein, a luminescent protein, a non-protein fluorophore, a non-protein chemiluminescent compound, or a fluorescent nanocrystal. The RET acceptor can be a molecule which quenches a signal from the RET donor, and in some embodiments displays an increased, sensitized acceptor signal. In order to increase the intensity of the optical signal, multiple RET donors and acceptors can also be included on each sensor construct. The sensor construct itself can be a polypeptide, and can comprise an antibody or antibody fragment such as a Fv portion of an antibody. In such embodiments, the molecular recognition domain is a CDR region of the Fv portion of the sensor construct. The molecular recognition domain can alternatively comprise a metal, such as a chelated metal, or an oligonucleotide.

In some embodiments of the sensor construct, the molecular scaffold, the molecular recognition domain, and/or the labels can be provided as separate molecules and then combined to form the sensor construct. For example, the molecular scaffold can comprise a heterodimeric coiled coil polypeptide pair and the molecular recognition domain can comprise the binding domain of a Fv fragment of an antibody (comprising a $V_H$ and a $V_L$ fragment). The molecular recognition domain in this embodiment can also be a chelated metal, an oligonucleotide, a peptide, a biotin molecule, or a non-peptide enzyme substrate/inhibitor molecule. The different components of the sensor construct in such embodiments are self-assembling when brought into contact with one another and allow Förster resonance energy transfer from the RET donor to the RET acceptor to occur.

DRAWINGS

These and other features, aspects and advantages of the present invention will become better understood with regard to the following description, appended claims, and accompanying figures where:

Figure 1:
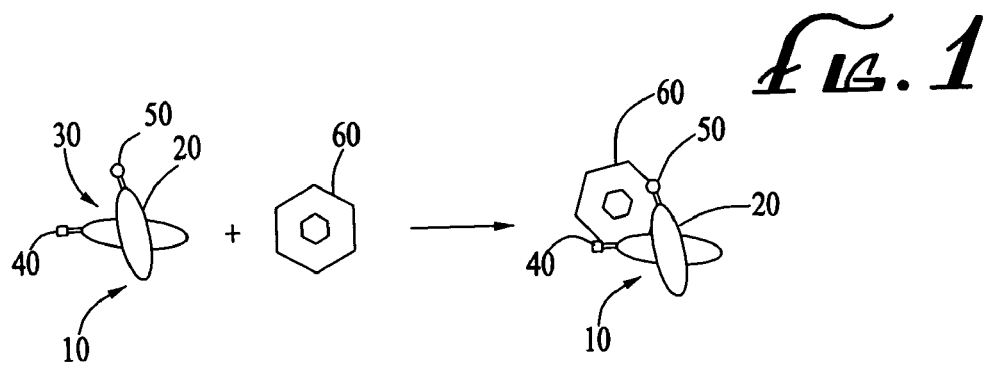
FIG. 1 illustrates the binding of an analyte to a sensor construct according to the present methods.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

The present sensor constructs allow the detection of an analyte by interfering with a Förster resonance energy transfer (FRET) interaction between two labels. When the sensor construct binds the analyte, such interference results in an optical signal of changed intensity which can be detected by sensitive ratiometric or fluorescence lifetime measurements. Because the present sensor constructs generate a detectable signal upon binding to an analyte, they are self-signaling, which is an advantage over many current detection assays in which additional signal-generating elements must be included in order to detect an analyte. In addition, it is not necessary to attach the present sensor constructs to a solid support, so that the present methods can be performed in solution as a noncompetitive assay and provide increased assay throughput.

Definitions

As used herein, the following terms have the meanings given below, unless a different meaning is clearly intended by the context in which such term is used.

"Analyte" refers to a molecule, compound, or other component in a sample. Analytes can be peptides, proteins, polynucleotides, organic molecules, sugars or other carbohydrates or carbohydrate polymers, lipids, or other types of molecules, including vitamins, hormones, and disease markers. Analytes can occur in combination with and/or as portions of other molecules. Analytes preferably do not include RET donors or RET acceptors.

"Antibody" refers to an immunoglobulin protein which specifically binds to an analyte. Antibodies include various classes and isotypes of immunoglobulins, such as IgA, IgD, IgE, IgG1, IgG2a, IgG2b, IgG3, and IgM. "Antibody fragments" refer to molecules such as Fab, scFv, F(ab')$_2$, and Fab' molecules comprising portions of intact antibodies. "Antibody derivatives" refer to antibodies or fragments thereof having additions or substitutions, such as chimeric antibodies. Antibodies, antibody fragments, and antibody derivatives can be derived from human or animal sources, from hybridomas, through recombinant methods, or in any other way known to the art.

"Epitope" refers to a localized region or regions on the surface of an analyte to which a molecular recognition domain specifically binds.

"Fluorescence" refers to the emission of light from a substance caused by exposure to electromagnetic radiation (generally in the visible range) from an external source, such as a laser. For purposes of this definition, fluorescence includes phosphorescence, defined as the continued emission of light by a substance after the exciting radiation has been discontinued.

"Förster Radius" refers to the distance at which resonance energy transfer between a RET donor and RET acceptor is 50% efficient (i.e. the spectral emission of 50% of excited donors is dimmed by a FRET interaction).

"FRET," "FRET interaction," and similar terms refer to Förster resonance energy transfer between a RET donor and a RET acceptor, as well as to similar types of energy transfer not strictly following the Förster's theory, such as the nonoverlapping energy transfer when nonoverlapping acceptors are utilized (see, e.g., Anal. Chem.2005, 77: 1483-1487).

"FRET ratio" (denoted by the symbol "R" in FIGS. 7A-7I) refers to the ratio of steady-state fluorescence intensities of a fluorescent RET donor and a fluorescent RET acceptor at their respective emission peaks when a sensor construct is excited at the optimal RET donor excitation wavelength ($\lambda_{max}$). "Label" refers to a molecule or moiety capable of providing a detectable signal. In the present sensor constructs and methods, the labels are RET donors or RET acceptors and the signal is an electromagnetic (e.g., optical) signal.

"Luminescence" refers to the production and emission of light from a nonthermal source, i.e. other than a hot, incandescent body. Among the several types of luminescence are chemiluminescence and bioluminescence, which are produced, respectively, by chemical and biochemical reactions. Luminescence does not include fluorescence.

"Moiety" refers to a portion of a molecule having a property of interest.

"Molecular recognition domain" or "MRD" refers to a molecule or moiety which is able to specifically bind an analyte. Examples of MRD's include antibody binding domains (i.e., CDR regions), antigen epitopes (e.g., when detecting antibodies), chelated metals, oligonucleotides, peptides and hormone receptors.

"Molecular size" with respect to a globular protein or peptide refers to the hydrodynamic radius of the molecule.

"Oligonucleotide" refers to a chain of between 5 and 200 nucleotides, generally between about 20 and 100 nucleotides, and more preferably about 30 nucleotides.

"Peptide" refers to a molecule comprising 50 or fewer linked amino acids.

"Polynucleotide" refers to a molecule comprising two or more linked nucleic acids. Polynucleotides include nucleic acids as well as nucleic acid molecules having substitutions and additions.

"Polypeptide" refers to a molecule comprising two or more linked amino acids.

"Protein" refers to a molecule comprising more than 50 linked amino acids.

"Ratiometric methods" refer to methods which measure the ratio of fluorescence from a RET donor and a RET acceptor in order to determine the amount of an analyte in a sample. Ratiometric measurements can be conducted with fluorometers.

"RET donor" refers to a fluorescent or luminescent moiety or molecule which is able to interact with a RET acceptor via Förster resonance energy transfer.

"RET acceptor" refers to a moiety or molecule which is able to interact with a RET donor via Förster resonance energy transfer, through enhanced fluorescence of the RET acceptor and/or quenching of a signal from the RET donor.

"Sensor construct" refers to a molecule, or to a collection of molecules comprising subunits which function together, which is capable of providing a detectable signal indicating the presence of an analyte in a sample as a result of the binding of the analyte to the sensor construct.

"Specific binding" or "specifically bind," with respect to the interaction between an analyte and a molecular recognition domain, refers to the attachment of the molecular recognition domain to the analyte and not to other components of a sample under the conditions of a particular assay. A relatively small amount of non-specific binding by a MRD can be tolerated in some assays, though this will need to be accounted for in interpreting assay results in order to avoid false positive results or inaccurate quantitative data. A molecular recognition domain can bind a particular group or class of molecules in some cases and still be regarded as specifically binding such molecules, such as when the MRD binds an epitope common to the group of molecules. The binding of an analyte by a molecular recognition domain can be reversible, i.e. the analyte can be detached from the specific binding partner without structurally altering the analyte or the specific binding partner, or can be irreversible such as the binding between biotin and avidin.

"Specific epitope binding," "specifically binding an epitope," and similar terms refer to the attachment of a molecular recognition domain to a specific epitope of an analyte. Such binding occurs only between a molecular recognition domain and the specific epitope, though a small amount of non-specific binding can be tolerated in some assays, for example the binding of an oligonucleotide to another oligonucleotide having several mismatched bases, or the binding of an antibody binding domain to an isoform of an analyte. Specific epitope binding excludes binding interactions which can occur between an analyte and a number of different molecules, such as ionic binding between a chelator and any of a number of different metals. A molecular recognition domain can however be described as exhibiting specific epitope binding if it binds the same epitope on a particular group or class of molecules. For example, the MRD can be directed against the Fc region of a class of antibodies and thereby specifically bind a number of different antibodies of that particular class.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

FRET

Förster resonance energy transfer is the physical principal utilized in the present methods to detect analytes. FRET involves the transfer of energy from a RET donor, normally a fluorescent or luminescent moiety in its excited state, to another excitable moiety, a RET acceptor, by a nonradiative dipole-dipole interaction. RET donor and acceptor pairs are chosen for the present sensor constructs so as to ensure that a FRET interaction is possible between the donor and acceptor. The donor's emission spectrum should generally have a shorter wavelength than the acceptor's emission spectrum (i.e. the donor's optimal emission wavelength maximum, $\lambda_{max}$, should be shorter than the acceptor's). In classical FRET, the emission spectrum of the donor and the absorption spectrum of the acceptor must overlap to some extent. There are, however, exceptions to the rule as in the case of anti-Stokes' shift FRET based on lanthanide chelate donors and nonoverlapping acceptors (see, e.g., Anal. Chem. 2005 Mar 1;77(5):1483-7).

In addition, the RET donor and RET acceptor must be positioned in close proximity on the sensor construct in order for a FRET interaction to take place. Generally, FRET is seen to occur when the donor and acceptor are separated by less than 10 nanometers, but FRET has also been detected at a molecular distance as high as 25 nanometers between the donor and acceptor (see, e.g., J. Am. Chem. Soc. 2005 Mar. 9;127(9):3115-3119). According to Förster's theory, the energy transfer efficiency also depends on the refractive index of the media between the donor and acceptor, the rate constant for fluorescence/luminescence emission by the energy donor, and the quantum yield of the donor in the absence of the acceptor. The intensity of an optical signal generated by a FRET interaction between a RET donor and RET acceptor of the present sensor construct depends on the identity of the donor and acceptor, as different donor and acceptor pairs have different Förster radii.

When a RET donor is in the excited state and a FRET interaction takes place between the donor and an acceptor, the fluorescence or luminescence of the donor is quenched (i.e., reduced in total light output). For some RET acceptors, light emission is triggered by energy absorbance or transfer from a RET donor, resulting in a light emission by the acceptor. Other acceptors, known as quenchers, dissipate the energy absorbed from a RET donor and do not emit light (or do so weakly).

A FRET interaction in the present methods can be detected by measuring the steady-state or time-resolved fluorescence or luminescence of the sensor construct using standard techniques known to the art (see, e.g., Curr. Opin. Chem. Biol. 2003 Oct; 7 (5):635-40). For example, the fluorescence of the RET acceptor or the quenching of RET donor fluorescence of luminescence, or both, can be measured. When a quencher is used as the RET acceptor, the quenching of the donor's emission is generally measured. In the present methods, the interference with an expected FRET interaction between a RET donor and RET acceptor indicates the presence of an analyte in a sample.

Sensor Construct Components

As shown in FIG. 1, the present sensor constructs 10 include three primary elements, namely a molecular scaffold 20, a molecular recognition domain 30, and a pair of labels 40, 50 which can interact via Förster resonance energy transfer. The labels 40, 50 are secured to the molecular scaffold 20 so as to be in close enough proximity to be able to interact via Förster resonance energy transfer in the absence of an analyte 60 bound to the MRD 30 of the sensor construct 10. The molecular recognition domain 30 is incorporated into or otherwise secured to either the molecular scaffold 20 or to one of the labels (40 or 50) such that binding of an analyte 60 to the MRD 30 interferes with a Förster resonance interaction between the pair of labels 40, 50. As shown in FIG. 1, when the MRD 30 binds the analyte 60, the analyte in one embodiment becomes interposed between the two labels 40, 50.

Molecular Recognition Domains

A number of different types of MRD's can be used in the present sensor constructs, depending on the analyte to be detected. In one embodiment, the MRD is the binding domain of an antibody, i.e. the CDR region. In some cases, a portion of a CDR region, such as a CDR3 portion of an antibody, can function as a MRD. When an antibody binding domain is the MRD, it can be part of a complete antibody, in which case antibodies directed against a single epitope of an analyte are preferably used. Such antibodies can be monoclonal antibodies produced through the use of hybridoma techniques or can be produced by recombinant methods, as is known to the art. Alternatively, polyclonal antibodies can also be used as MRD's to detect an analyte.

MRD's can also be included in antibody fragments which retain their specific binding characteristics. Such fragments can be, for example, antibody fragments lacking the Fc portion of an antibody, e.g., Fab, Fab' and F(ab')$_2$ fragments. Fab and F(ab')$_2$ fragments can be produced by methods known to the art, e.g. by cleaving a monoclonal antibody with proteolytic enzymes such as papain, trypsin, ficin, and/or pepsin. Fab' fragments can be produced by reductive cleavage of F(ab')$_2$ fragments with agents such as dithiothreitol or mercaptoethanol. Single chain Fv (scFv) antibodies, which incorporate the entire antibody binding region in a single polypeptide chain, can likewise be obtained through reductive cleavage of the disulfide bonds connecting the heavy chain components of an intact antibody. In a preferred embodiment, antibody fragments are alternatively produced using recombinant techniques.

MRD's comprising the binding portion of an antibody can be incorporated into a molecular scaffold in a number of ways. In one embodiment, an antibody or portion thereof comprising an antibody binding domain is produced independently of the molecular scaffold and is then attached to the scaffold. For example, an antibody having a biotin moiety can be attached to a molecular scaffold having an avidin moiety attached at an appropriate location. In a preferred embodiment, the molecular scaffold comprises a recombinantly produced protein, and the MRD is the binding portion of an antibody which is incorporated into the molecular scaffold. In this way the molecular scaffold and MRD can be produced together and no additional step to attach the MRD to the molecular scaffold is required.

In an alternative embodiment, the MRD can be a chelated metal, such as nickel, for capturing a metal-binding agent. In this embodiment, the metal is preferably bound to the molecular scaffold by being chelated to the sensor construct via a metal-chelating group (such as nitrilotriacetic acid) chemically coupled to the molecular scaffold or the labels. Preferably, the analyte to be detected is a peptide or protein to which a His-tag, i.e. a chain of multiple histidine residues (usually five or six) near the N- or C-terminus of the peptide or protein, has been attached.

The MRD can alternatively be a peptide that binds other polypeptides or even non-peptides. Current combinatorial peptide library screening techniques allow the selection of unique peptides that bind a variety of molecules (see, e.g., Science. 1990 Jul. 27; 249(4967): 404-6). A peptide MRD can be incorporated into the molecular scaffold or the labels of the sensor construct.

The MRD can also comprise other types of specific binding molecules. For example, the MRD can be an oligonucleotide for detecting a polynucleotide having a complementary sequence. Certain DNA/RNA MRDs, termed aptamers, can bind proteins and thus potentially be useful for detecting protein analytes. MRD's can also comprise moieties that are typically regarded as antigens for immunoassays, in order to detect the presence, for example, of an antibody in a sample. The sample can comprise plasma or blood in one embodiment and the MRD can be a peptide epitope against an anti-HIV antibody in order to detect the presence of anti-HIV antibodies.

One of skill in the art will appreciate that either member of a specific binding pair (such as an antibody and antigen) can comprise a molecular recognition domain. Specific binding pairs include carbohydrate and lectin; biotin and avidin; folic acid and folate binding protein; vitamin B12 and intrinsic factor; and Protein A or Protein G and immunoglobulin.

Labels

A variety of labels can be used in the present sensor construct as the RET donor and/or the RET acceptor. Both the RET donor and RET acceptor can be fluorescent labels, which include such dyes as fluorescein, rhodamine, coumarin, and derivatives thereof. It is also possible to use lanthanide (rare-earth elements) atoms as donors and conventional organic dyes as acceptors in FRET (see, e.g., Nat. Struct. Biol. 2000 Sep. 7(9):730-4).

Further fluorescent dyes are listed in Table 1 below, all of which are commercially available (e.g., from Sigma Chemical, St. Louis, Mo.).

TABLE 1

| Fluorescent Labels | |
|---|---|
| 4-acetamido-4'-isothiocyanatostilbene-2-2'-disulfonic acid | 5-(4,6-dichlorotriazin-2-yl)aminofluorescein (DTAF) |
| 7-amino-4-trifluoromethylcoumarin | N-(4-anilino-1-naphthyl)maleimide |
| 4',6-diamidino-2-phenylindole (DAPI) | 7-amino-4-methylcoumarin (AMC) |
| 4,4'-dilsothiocyanatostilbene-2,2'-disulfonic acid | tetramethylrhodamine isothiocyanate (TRITC) |
| quinolizino fluorescein isothiocyanate (QFITC) | dansyl chloride |
| eosin isothiocyanate | erythrosin B |
| fluorescamine | fluorescene |
| fluorescein derivatives | 4-methylumbelliferone |
| o-phthaldialdehyde | rhodamine B and derivatives |
| rhodamine 6G | rhodamine 123 |
| sulforhodamine B | sulforhodamine 101 |
| sulforhodamine 101 acid chloride | |

Fluorescent labels also include fluorescent proteins, such as green fluorescent protein (GFP). GFP is a spontaneously fluorescent protein isolated from the jellyfish *Aequoria victoria*, and a number of GFP variants (both blue-shifted and red-shifted) have been developed. Such variants or derivatives comprise molecules with substitutions, additions, and/or deletions to the native GFP sequence. GFP variants include BFP (blue), CFP (cyan), and YFP (yellow), as well as enhanced variants of these molecules such as EGFP, ECFP and EYFP. When GFP is one of the fluorophores, rhodamine or Marina Blue (Molecular Probes, Eugene, Oreg.) are advantageously employed as the other partner of the FRET pair. Additionally, a number of red fluorescent proteins (RFP) from reef coral species and their engineered variants can also be used.

Fluorescent proteins are advantageously employed as RET donors and acceptors in the present sensor constructs when the MRD and/or the molecular scaffolds are produced recombinantly. In this case, the RET donor and RET acceptor can be produced together with the molecular scaffold and/or the MRD as a single polypeptide molecule, and the placement of the RET donor and acceptor on the molecule can be precisely controlled.

Other fluorescent compounds which can be used as labels in the present sensor constructs include nanocrystals, also referred to as quantum dots. Quantum dots (QDs) are semiconductor nanocrystals whose fluorescence emission wavelength is proportional to the size of the crystal. Quantum dots have a diameter on the order of the compound's Exciton Bohr Radius, and are generally between 2 and 10 nanometers wide. They typically comprise compounds formed from two elements, one from each of two Periodic Table groups, namely from Periodic Table Groups 2 and 6, Periodic Table Groups 3 and 5, or Periodic Table Groups 4 and 6. Exemplary materials include CdSe, ZnS, and PbSe. The outer surface of a quantum dot can be readily conjugated to organic molecules to facilitate attachment to other moieties, such as to the molecular scaffold of the present sensor construct.

In some embodiments, the RET donor of the sensor construct can comprise a luminescent moiety instead of a fluorescent moiety. For example, the RET donor can comprise luciferase, which produces light when it acts on its substrate, coelenterazine. Fluorescent molecules such as YFP and GFP can act as RET acceptors with luciferase. The use of biologically derived compounds such as luciferase or aequorin as a RET donor is sometimes referred to as BRET (Bioluminescence Resonance Energy Transfer).

Other luminescent moieties, such as chemiluminscent moieties, can also be used as RET donors. For example, luminol (5-amino-2,3-dihydro-1,4-phthalazine-dione) is a chemiluminescent compound which emits a green-blue light when exposed to a basic solution such as a perborate, permanganate, hyperchlorite, iodine, or hydrogen peroxide which oxidizes luminol. Other luminescent moieties include peroxyoxalate chemiluminophores such as bis(2,4,6-trichlorophenyl)oxlate (TCPO) and bis(2-(3,6,9-trioadecanyloxycarbonyl)-4-nitrophenyl)oxalate (TDPO).

In addition, quenchers can be used as the. RET acceptors for some embodiments of the present methods. The use of quenchers such as DABCYL, BHQ, or QSY dye (e.g., QSY 7, QSY 9, QSY 21, QSY 35, available from Molecular Probes, Eugene, Oreg., USA) has the advantage of eliminating the potential problem of background fluorescence resulting from direct (i.e., non-FRET) acceptor excitation.

Molecular Scaffolds

The molecular scaffolds of the present invention are adapted to bind a RET donor, RET acceptor and a MRD and to maintain these moieties in a particular spatial relationship with respect to one another. The RET donor and RET acceptor must be within a distance which allows a Förster resonance energy interaction between the donor and acceptor in the absence of an analyte bound to the MRD. The RET donor, RET acceptor, and MRD should also be retained in the correct dipole orientation to facilitate FRET interactions (see, e.g., Stryer L., Fluorescence energy transfer as a spectroscopic ruler, Annu. Rev. Biochem., 47:819-46 (1978)). The MRD is further preferably retained by the molecular scaffold so that when it binds an analyte, the analyte bound by the MRD or at least a portion thereof is interposed between the RET donor and the RET acceptor, thereby interfering with Förster resonance energy interactions between the donor and acceptor. It is not required to have a conformational change in the molecular scaffold in the present sensor construct to enable detection of the analyte.

A variety of different molecules capable of binding labels and MRD's can be used as molecular scaffolds in the present sensor construct. For example, peptides, proteins, carbohydrates, and organic molecules, as well as molecules comprising a combination of such molecules such as nucleic acids, can be used as the molecular scaffold moiety of the present sensor construct. In one embodiment, the molecular scaffold is a protein comprising an antibody, antibody fragment, or antibody derivative, such as a Fv moiety. The Fv moiety comprises a VH and a VL fragment which are preferably stabilized by a flexible linker to form a single-chain Fv (scFv), or by heterodimeric coiled coils to form helix-stabilized Fv (hsFv).

In another embodiment, the molecular scaffold comprises a protein such as a periplasmic binding protein. One such protein is maltose binding protein (MBP). When labels such as GFP and YFP are attached, respectively, to the N- and C-termini of MBP, they are capable of interacting via Förster resonance energy interaction.

When using a periplasmic binding protein such as MBP or other similar protein which changes conformation upon binding to a small molecule as a molecular scaffold, it is possible to make use of such conformational change to enhance the sensitivity of the present assay, although such conformational change is not a prerequisite for analyte detection using the present sensor construct. In the presence of maltose, MBP undergoes a hinge-bending like conformational change, which can bring a RET donor and RET acceptor into closer proximity, resulting in a detectable FRET interaction. In the presence of a target analyte that binds the MRD, however, this FRET effect is reduced.

Other types of molecular scaffolds can also be used to form the present sensor constructs. For example, heterodimeric coiled coils can be used to present the MRD and the labels. Alternatively, rigid linkers comprising organic compounds such as those described in U.S. Pat. No. 5,945, 526 can be used to retain a RET donor, RET acceptor, and MRD. Polynucleotide molecules can also be used as molecular scaffolds.

Coupling of Labels

The RET donor, RET acceptor, and MRD can be attached to the molecular scaffold in a variety of ways, depending on the type of molecular scaffold. When the molecular scaffold and/or the MRD is a protein produced through recombinant methods, fluorescent or luminescent proteins (such as GFP and luciferase) can be advantageously incorporated into the recombinant protein and produced together with the molecular scaffold or MRD as a single molecule. For example, a hexa-histidine tag can be included in a protein comprising the molecular scaffold or MRD. This not only allows convenient metal-affinity purification of the sensor construct, but the His-tag can also then be labeled with a Ni-NTA conjugated fluorophore (see, e.g., Kapanidis AN, Ebright YW, Ebright RH, Site-specific incorporation of fluorescent probes into protein: hexahistidine-tag-mediated fluorescent labeling with (Ni(2+):nitrilotriacetic Acid (n)-fluorochrome conjugates, J. Am. Chem. Soc. 2001 Dec. 5;123(48):12123-5).

Another method for the site-specific labeling of proteins involves cysteine-specific labeling with thiol-reactive reagents. Site-directed mutagenesis can be used to introduce an N-terminal cysteine into a protein such as a scFv moiety (see, e.g., Gentle et al., Direct production of proteins with N-terminal cysteine for site-specific conjugation, Bioconjug. Chem., 15:658-663 (2004)). Site-specific labeling of the amino terminus of a scFv moiety can then be achieved using chemical ligation techniques to incorporate a thiol-reactive fluorescence or quencher probe (see, e.g., Dawson, et al., Synthesis of proteins by native chemical ligation, Science, 266:776-779(1994)). A wide variety of thiol-reactive fluorophores are available commercially. Alternatively, thiol-reactive fluorescent oligonucleotide probes can be made using commercially available kits to introduce multiple copies of fluorophores into a thiol-reactive oligonucleotide, and such thiol-reactive fluorescent oligonucleotide probes can be used to label a cysteine moiety such as a N-terminal cysteine (see, e.g., Tung, CH and Stein, S, Preparation and applications of peptide oligonucleotide conjugates, Bioconjug. Chem., 11:605-618 (2000)).

When the molecular scaffold comprises an antibody, antibody fragment, or antibody derivative, labels can be specifically attached through the use of specific binding moieties such as Protein L, Protein A, and/or Protein G. Protein L (originally isolated from *Peptostreptococcus magnus*) binds to the framework region of the immunoglobulin light chain (VL). A single domain of Protein L (PpL) also shows strong binding to the framework region of VL, and can bind VL without affecting antigen binding. The E domain of *Staphylococcal* Protein A (SPA-E) binds strongly to the framework region of VH, also without affecting analyte binding. The amino termini of the VL and VH domains are within a distance that permits FRET to occur (between about 3 and 4 nm), and so are appropriate places to bind labels to construct a sensor construct.

In this embodiment, PpL and SPA-E can be expressed in *Escherichia coli*, purified, and respectively labeled with a RET donor and an acceptor. When contacted with an antibody, antibody fragment, or an antibody derivative, the labeled PpL and SPA-E molecules become bound, thereby labeling such molecules. Other methods of attaching labels to a molecular scaffold are also possible. For example, labels can be attached to molecular scaffolds using conventional chemical coupling reactions, resulting in covalent attachment of the label to the molecular scaffold.

When the molecular scaffold is a polynucleotide, labels can be directly incorporated into the sequence of the polynucleotide during synthesis using dye-phosphoramidites, which are substituted for nucleotide phosphoramidites during synthesis. Other ways of incorporating fluorescent dyes into polynucleotides are also known to the art.

Figure 3:
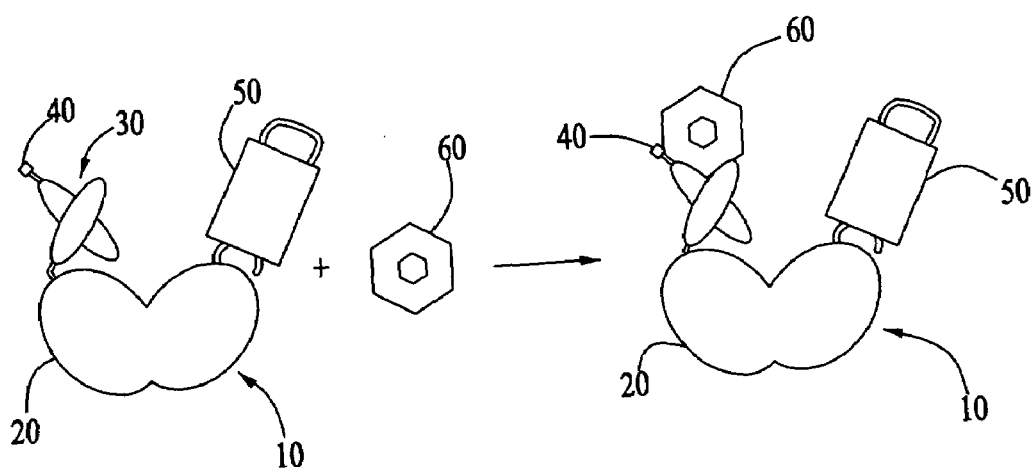
FIG. 3 illustrates the binding of an analyte to a further alternative embodiment of the present sensor construct.

As shown in FIG. 3, labels (i.e. label 40 in FIG. 3) can also be attached to a MRD 30 directly, rather than being attached directly to a molecular scaffold, as long as such attachment does not interfere with analyte binding by the MRD. Such attachment also must not interfere with a FRET interaction between the RET donor and RET acceptor prior to the binding of an analyte by the MRD 30.

Figure 4:
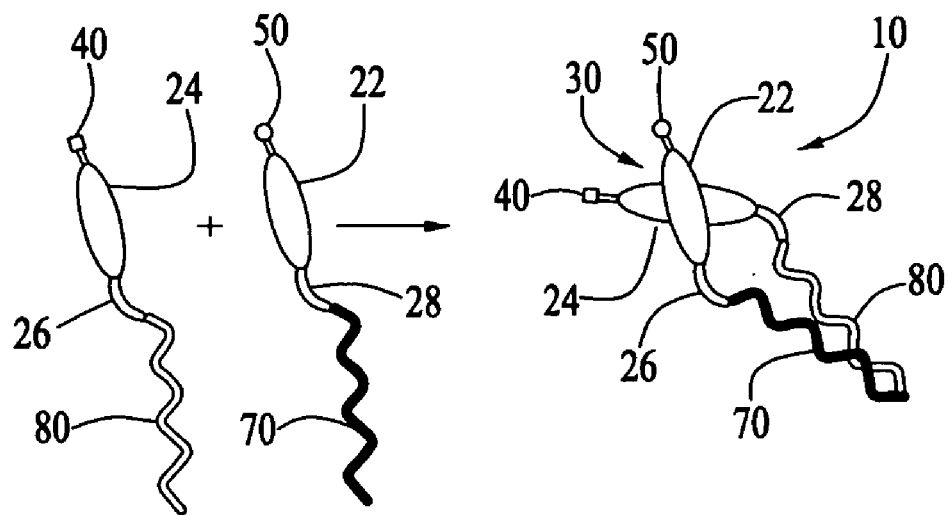
FIG. 4 illustrates a further alternative embodiment of the present sensor construct in which the MRD is self-assembling.
Figure 4A:
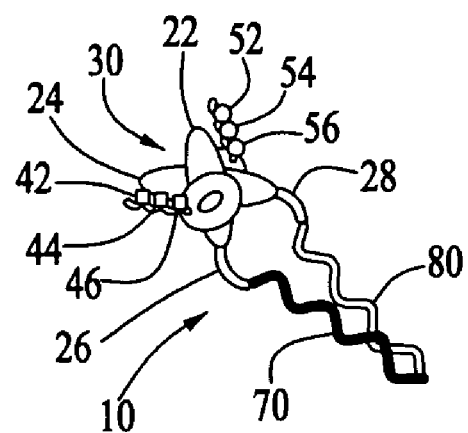
FIG. 4A illustrates an embodiment of the sensor construct depicted in FIG. 4 in which the labels are also self-assembling.

In some embodiments, it can be advantageous to include a plurality of donor RET moieties and/or a plurality of RET acceptor moieties in a sensor construct. As shown in FIG. 4A, multiple RET donors 42, 44, and 46 are provided on the label 40 while multiple RET acceptors 52, 54, and 56 are provided on RET acceptor 50. The use of multiple RET donors and acceptors in a sensor construct 10 can increase the intensity of an optical signal produced by the present sensor constructs.

Sensor Constructs

A wide variety of molecular recognition domains, labels, and molecular scaffolds can be combined to form the present sensor constructs. When designing polypeptide sensor constructs as described herein, molecular modeling tools such as Deep View/Swiss PDB Viewer (available at http://www.expasy.org/spdbv/) can be used for protein structure viewing and manipulation. Programs such as Dock 5.0 (available from the Molecular Design Institute, University of California, San Francisco) can be used for molecular docking, and InterPreTS (available at http://www.russell.embl.de/interprets/) can be used for analyzing protein interactions. Protein structures for use with such tools can be obtained, for example, from RCSB Protein DataBank (available at http://pdbbeta.rcsb.org/pdb/).

Figure 2:
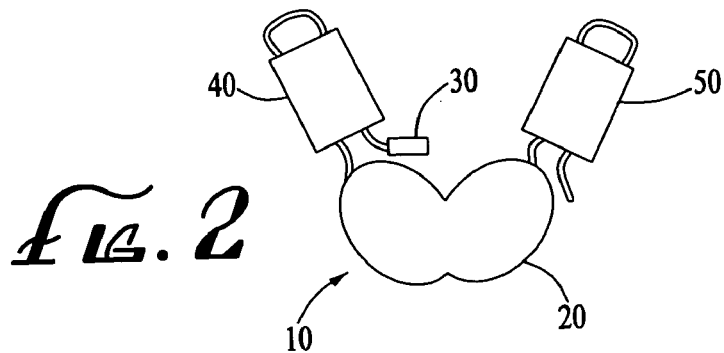
FIG. 2 illustrates an alternative embodiment of the present sensor construct in which the MRD is attached to a label.
Figure 2A:
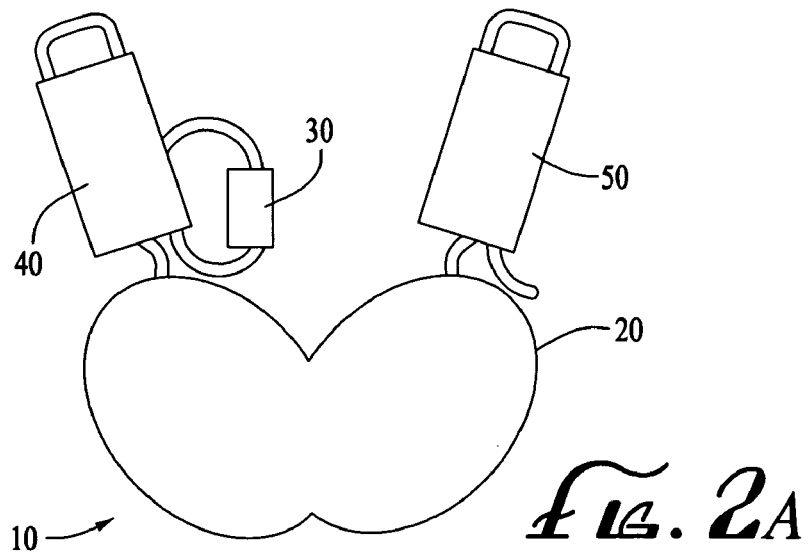
FIG. 2A illustrates another embodiment of the present sensor construct in which the MRD is attached to a label.

In one embodiment, a MRD can be attached to one of the labels of the sensor construct. As shown in FIG. 2, MRD 30 is attached to the label 40. Advantageously, the label and the MRD are polypeptides, and are produced together as a single molecule. In the embodiment shown in FIG. 2, the MRD 30 is attached at the N-terminus of the label 40. In the illustrated embodiment the label 40 is attached to the N-terminus of a polypeptide molecular scaffold 20, which can be MBP. A further protein label 50 is attached to the C-terminus of the molecular scaffold 20. A similar embodiment is shown in FIG. 2A, in which the MRD 30 is a peptide loop inserted into the sequence of the polypeptide label 40.

In an alternative approach, shown in FIG. 3, the termini of a polypeptide molecular scaffold 20 (which can be maltose-binding protein) are respectively fused to a label 50 such as GFP and to a molecule comprising a polypeptide molecular recognition domain 30, such as a scFv or other antibody fragment, using recombinant DNA technology. The molecule comprising the MRD 30 is then labeled with a label 40, which can be a fluorophore such as rhodamine. MRD's comprising peptides and even protein domains can also be inserted at certain sites of the nucleotide sequence of MBP, and such fusion proteins can then be expressed recombinantly, without affecting the ability of MBP to bind maltose (see, e.g., Betton et al., Location of tolerated insertions/deletions in the structure of the maltose binding protein, FEBS Lett. 325(1-2):34-8 (1993) and Guntas Ostermeier, Creation of an allosteric enzyme by domain insertion, J Mol Biol. 336(1):263-73 (2004)). Alternatively, MRD 30 can be chemically coupled to specific locations of the MBP.

Figure 3A:
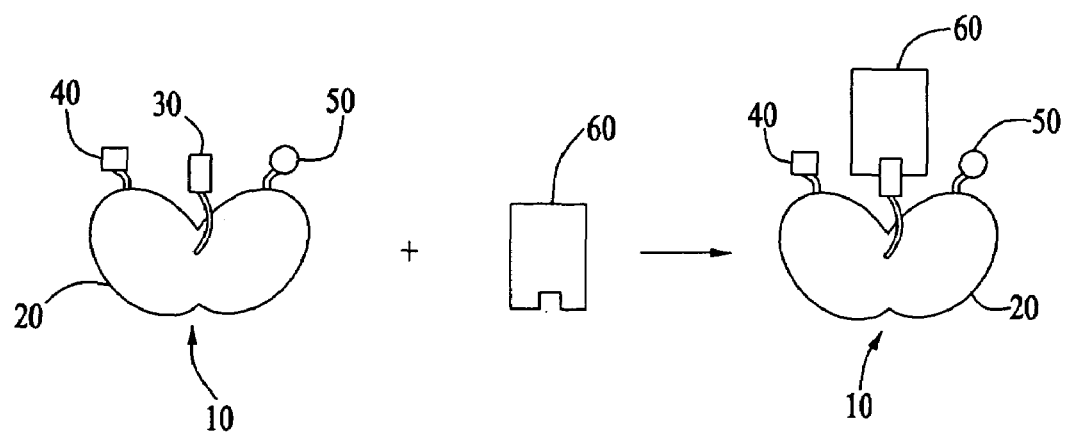
FIG. 3A illustrates the binding of an analyte to a yet another embodiment of the present sensor construct.

A further approach is illustrated in FIG. 3A. In this embodiment, the MRD 30 is attached to the molecular scaffold 20 directly. MRD's can be attached to a molecular scaffold as described above. FIG. 3A further shows the binding of an analyte 60 to the MRD 30.

In some embodiments of the present sensor constructs 10, the constructs can be formed from separate molecules which become attached to or associated with each other to form a sensor construct 10. For example, as shown in FIG. 4, the molecular scaffold 20 and/or the MRD 30 of the present sensor construct 10 can, in one embodiment, comprise two molecules which are produced separately and then assembled. This has the advantage of allowing a RET donor to be attached to one of the molecules and a RET acceptor to be attached to the other, so that the binding of the labels to portions of the molecular scaffold and/or the MRD can be better controlled. One way to create a self-assembling sensor construct from two separate molecules is to make use of heterodimeric coiled coil polypeptide moieties, such as WinZip-A2B1 (see, e.g., J Mol Biol. 2000 Jan. 21; 295 (3):627-39). As shown in FIG. 4, when a heterodimeric coiled coil moiety 70 such as WinZip-A2 is attached to one portion 22 of a molecular scaffold 20 and another coiled coil moiety 80 which specifically binds to the first coiled coil moiety 70 (such as WinZip-B1) is attached to the other portion 24 of the molecular scaffold 20, the coils 70 and 80 will associate, thereby joining the separate portions 22 and 24 of the molecular scaffold 20 to form the MRD 30. Such coils can be joined to the molecular scaffold portions via linkers, such as the short peptide linkers 26, 28 illustrated in FIGS. 4 and 4A.

One particular molecule comprising this embodiment is a helix-stabilized recombinant Fv, in which the CH1 and CL domain of a Fab fragment are replaced with a heterodimeric coiled coil (such as WinZip-A2B1 or an E/K coiled coil polypeptide). One portion of the molecular scaffold comprises the VH region of a Fv fragment attached to WinZipA2, while the other portion comprises a VL region attached to WinZipB1. Both portions can be produced by genetic fusion and standard recombinant methods known to the art. When the VH and VL portions are placed in contact with each other, they self-assemble to form a sensor construct.

Figure 5A:
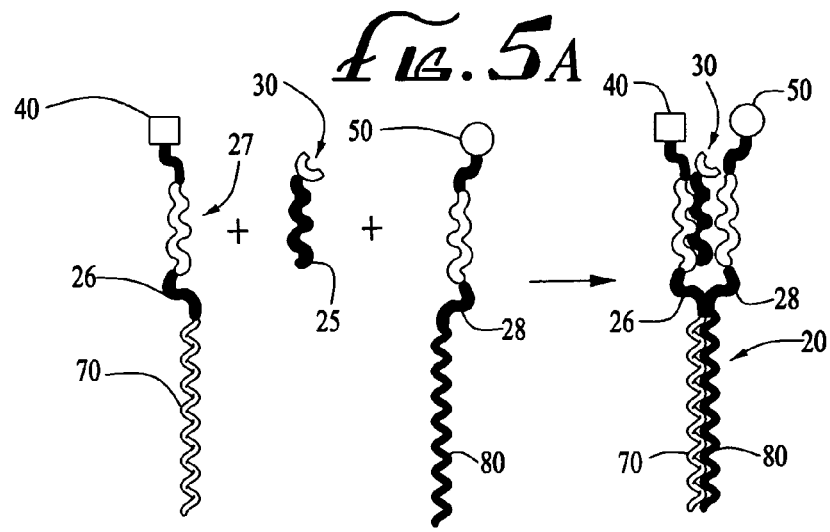
FIG. 5A illustrates the assembly of another self-assembling embodiment of the present sensor construct.
Figure 5B:
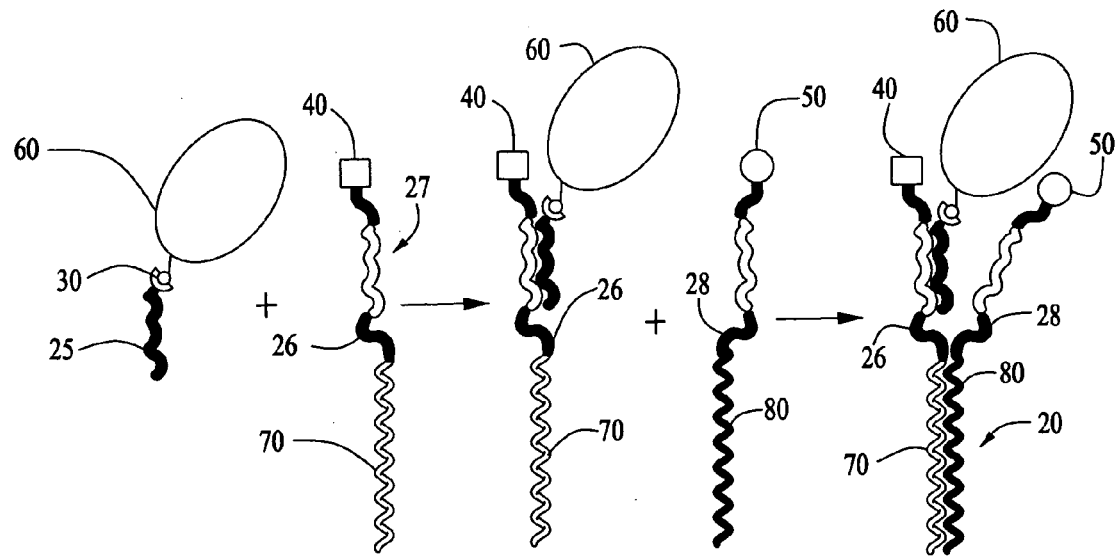
FIG. 5B illustrates the binding of an analyte to the sensor construct depicted in FIG. 5A.
Figure 6:
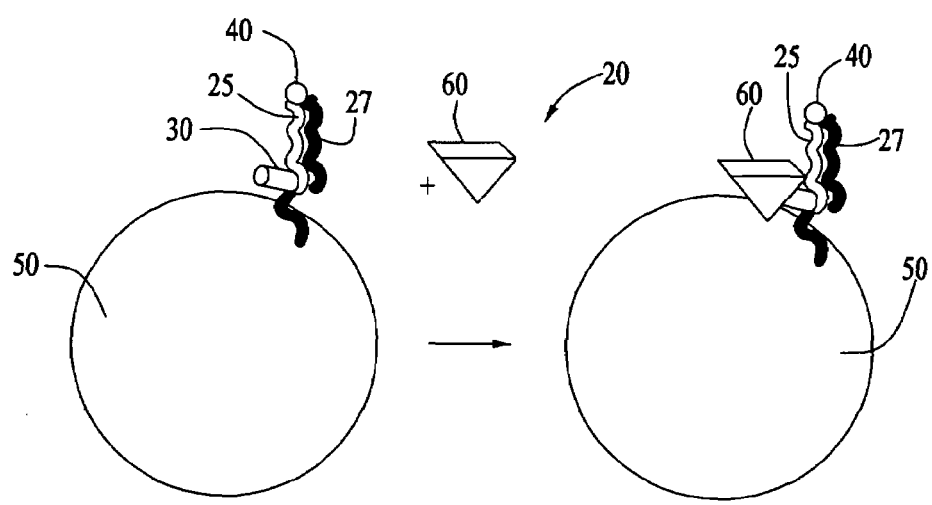
FIG. 6 illustrates an embodiment of the present sensor construct in which the molecular scaffold is self-assembling.

In related embodiments, shown in FIGS. 5A, 5B and 6, the molecular scaffold 20 can comprise two moieties which specifically bind to each other, such as coiled coil polypeptide pairs. In the embodiment shown in FIGS. 5A and 5B, a first coiled coil polypeptide partner 70 is attached to label 40 by means of a linker 26. Also included in this molecule is a specific binding region 27. A second coiled coil polypeptide partner 80 is attached to label 50 via linker 28, and when contacted with one another the two coiled coil partners specifically bind to each other. MRD 30 is attached to a partner 25 for the specific binding region 27 and likewise becomes associated with specific binding region 27 when contacted with it. As shown in FIG. 5B, when an analyte 60 comprising an epitope 62 to which the MRD 30 specifically binds is brought into contact with the separate molecules comprising this embodiment of the sensor construct 10, the analyte 60 bound to the MRD 30 becomes attached to the construct via binding partners 25, 27 and interferes or otherwise alters a FRET interaction between the labels 40 and 50.

In a further alternative embodiment of the present sensor construct 10, shown in FIG. 6, the MRD 30 can be attached to a first specific binding molecule 25 to which label 40 is also attached. A second label 50 (illustrated as a quantum dot in FIG. 6) is attached to a binding partner 27 for specific binding molecule 25. When contacted with one another, the specific binding partners 25, 27 associate to form the molecular scaffold 20.

Assay Methods

The present sensor constructs are adapted to detect large target analytes such as cells, viruses, antibodies, and proteins, in particular analytes having a molecular size in the range of between about 1 nm to about 25 nm, more preferably between about 3 nm and about 6 nm. The sensor constructs are therefore advantageously used in diagnostic assays. For example, a person suspected of possibly having a medical condition can be tested using the present sensor constructs by contacting a sample of material from the patient (such as saliva, urine, plasma, serum, blood, or other tissue) with a solution containing the present sensor constructs. The sensor constructs are adapted to bind an indicator of the condition which is suspected of being present in the sample. Upon detecting the binding of the indicator in the sample to the sensor construct at an appropriate level of signal intensity, the patient can be diagnosed as having the condition. Samples of experimental or manufactured materials which are purified or produced in aliquots or batches can also be tested to determine the presence of a desired material in a particular aliquot or batch. For example, fractions of the eluate from a chromatographic separation can be tested to detect which fractions contain an analyte of interest in solution. Other samples, such as environmental samples, can also be tested according to the present methods, for example to detect unwanted contaminants in such samples.

Preferably, the assays performed according to the present methods are non-competitive assays, and the sensor constructs produce a signal directly in response to binding an analyte. After contacting a sample with a sensor construct, an optical signal from the sensor construct is measured. If interference with a Förster resonance energy transfer interaction between the RET donor and the RET acceptor of the construct is detected, this indicates that the analyte of interest is present in the sample. Preferably, an optical signal is obtained from a solution containing the sensor construct prior to contacting it with a sample, in order to measure a control optical signal generated by a Förster resonance energy transfer interaction between the RET donor and the RET acceptor of the sensor construct. The difference between the control optical signal and an optical signal measured in a sample solution can be used to quantitatively determine the amount of analyte present in the sample. Ratiometric methods can be used to make this determination, as is known to the art. Changes in the intensity of the emissions from a sensor construct and/or in the decay kinetics of the optical signal emitted by the sensor construct can be measured for this purpose. Time-resolved methods can also be applied when RET donors with long lifetime such as lanthanides are used, as is known to the art.

One advantage of the present methods is that they can be performed in solution, without having to attach the sensor constructs to a solid support. This avoids the multiple binding and washing steps required in solid-phase assays such as conventional ELISA and hence assay throughput can be greatly increased, with less chance of operator error. If desired, the present constructs can also be attached to a solid support, such as a microtiter well or microarray. When the present sensor constructs are attached to a solid support, sensor constructs which are specific for different analytes can be localized in discrete locations on the solid support, for example in a microarray. The presence of a particular analyte in a sample will be indicated by the appropriate optical signal from the discrete location on the support where a sensor construct adapted to bind that analyte is bound. In this way, a single sample can be tested for the presence of multiple analytes.

A wide variety of solid supports can be used in this embodiment of the present methods. Suitable solid supports include plates, wells, membranes, and fibers. For example, the solid support can be a particle, microarray, microtiter well, waveguide, or capillary. The solid support can be made from any material to which the present sensor construct can be bound which doesn't interfere with analyte binding by the MRD or with a FRET interaction between the RET donor and RET acceptor. Suitable materials include nitrocellulose, glass, and a number of synthetic polymers, including nylon, polyvinylidene fluoride (PVDF), polystyrene, polypropylene, polycarbonate, polyglycidylmethacrylate, polyacrylamide, polyamide, and polyvinylchloride.

The present sensor constructs can be coupled to solid supports in ways known to the art. For example, if the solid support is a particle with a silica surface cyanosilane coupling agents can be used (see, e.g., Falipou et al., New use of cyanosilane coupling agent for direct binding of antibodies to silica supports, Bioconjug. Chem., 10:346-353

(1999)). For a microarray format, the sensor constructs can be spotted onto commercially available multi-well glass microarray slides. Wells can be created using a hydrophobic coating (available from Erie Scientific, Portsmouth, N.H.) using a pin-tool type microarrayer to create a microarray.

Various systems are known to the art for exciting fluorophores and for detecting and measuring optical signals produced by the present sensor constructs. For example, wide-field fluorescence microscopy and laser scanning confocal microscopy (LSCM) can be used.

Kits

In one embodiment, the present sensor constructs can be provided in kits for use in detecting analytes. For example, such a kit can include a polypeptide comprising an Fv portion of an antibody; a first label comprising a RET donor bound to a polypeptide comprising the E domain of Protein A; and a second label comprising a RET acceptor bound to a polypeptide comprising the binding domain of Protein L. When these separate components are combined in solution, the first label becomes bound to the VH portion of the Fv moiety via the Protein A domain, and the second label becomes bound to the VL portion of the Fv moiety via the Protein L domain. Alternatively, the first label can comprise a RET acceptor while the second label comprises a RET donor.

In a further embodiment, such a kit can include a first label comprising a RET donor linked to a heterodimeric coiled coil polypeptide and a second label comprising an RET acceptor and a heterodimeric coiled coil polypeptide which specifically binds to the coiled coil polypeptide of the first label. In this embodiment the kit also includes a molecular recognition domain carried on a molecular scaffold which specifically binds to either the first label, the second label, or to both, preferably via a linker.

EXAMPLES

Example 1

Detecting Anti-GFP Antibodies

A maltose binding protein construct was tested to verify the utility of the present methods. The construct (known as a fluorescence indicator protein, or FLIP) was based on the maltose binding protein. Attached to the N-terminus of the MBP moiety was ECFP (enhanced cyan fluorescent protein), and attached to the C-terminus of MBP was EYFP (enhanced yellow fluorescent protein). A hexa-histidine tag was further attached to the N-terminus of the construct. This construct, described in PCT International Patent Application No. WO 03/025220, was kindly provided by Professor Wolf Frommer of the Carnegie Institution of Washington.

Several different experiments were performed with this construct. The results are shown in FIGS. 7A-7I, which make use of the symbols described in Table 2 below.

TABLE 2

FIG. 7 Legends

| Symbol | Definition |
|---|---|
| $R_S$ | FRET ratio of the sensor protein |
| $R_{SA}$ | FRET ratio of the sensor protein upon binding to the target (antibody) |
| $R_{SAL}$ | FRET ratio of the sensor protein upon first binding to the target then to maltose |

TABLE 2-continued

FIG. 7 Legends

| Symbol | Definition |
|---|---|
| $R_{SL}$ | FRET ratio of the sensor protein upon binding to maltose |
| $\delta_A$ | $R_{SA} - R_S$ |
| $\delta_{AL}$ | $R_{SAL} - R_{SL}$ |

Figure 7A:
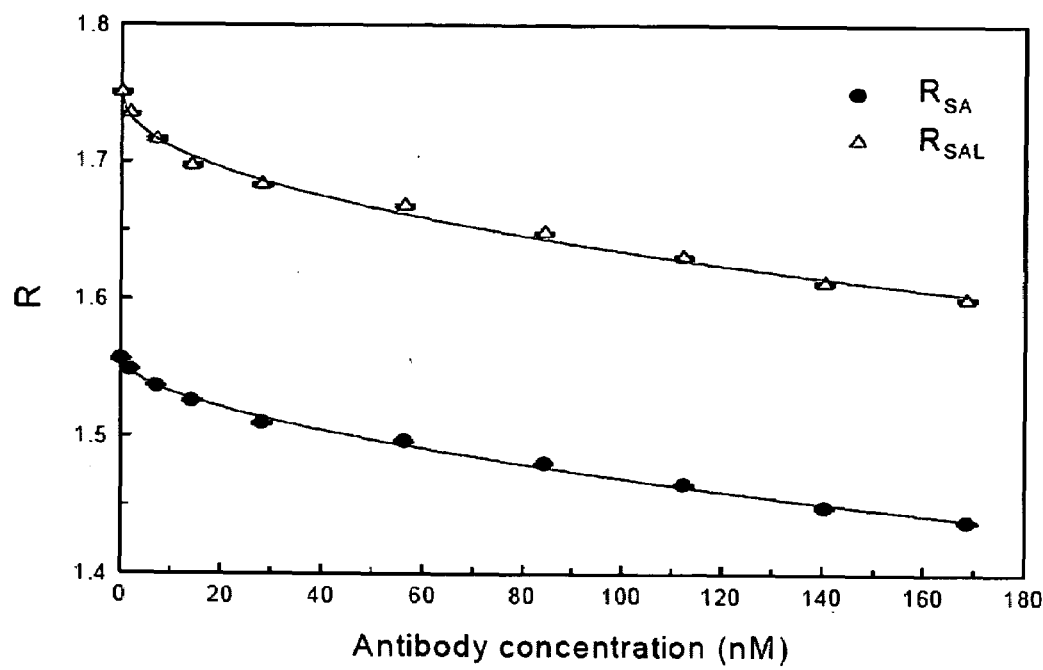
FIGS. 7A-7I are graphs depicting results of experiments performed according to the present methods.
Figure 7B:
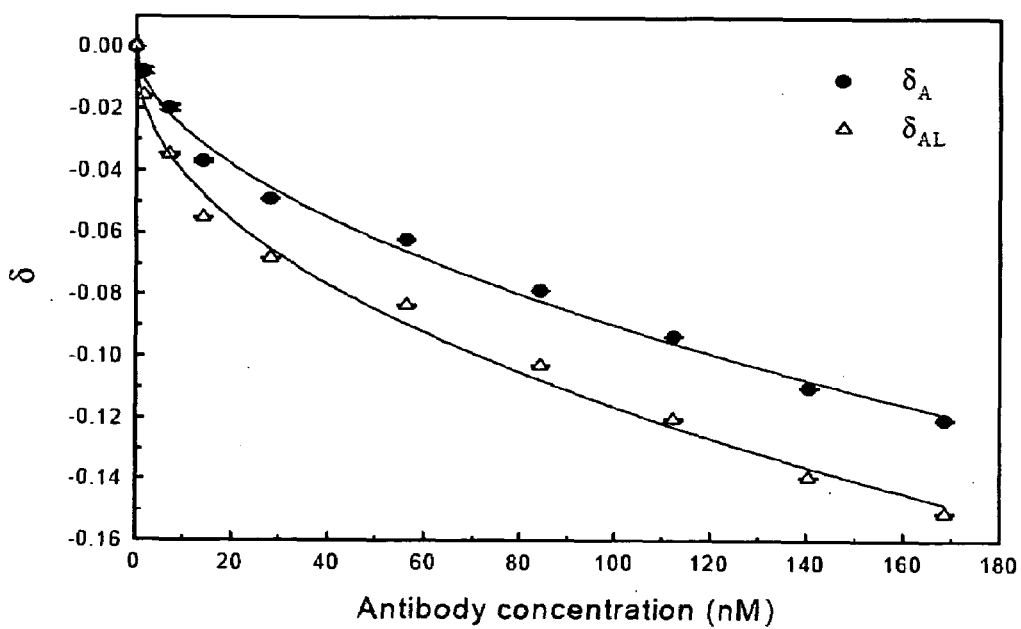
Figure 7C:
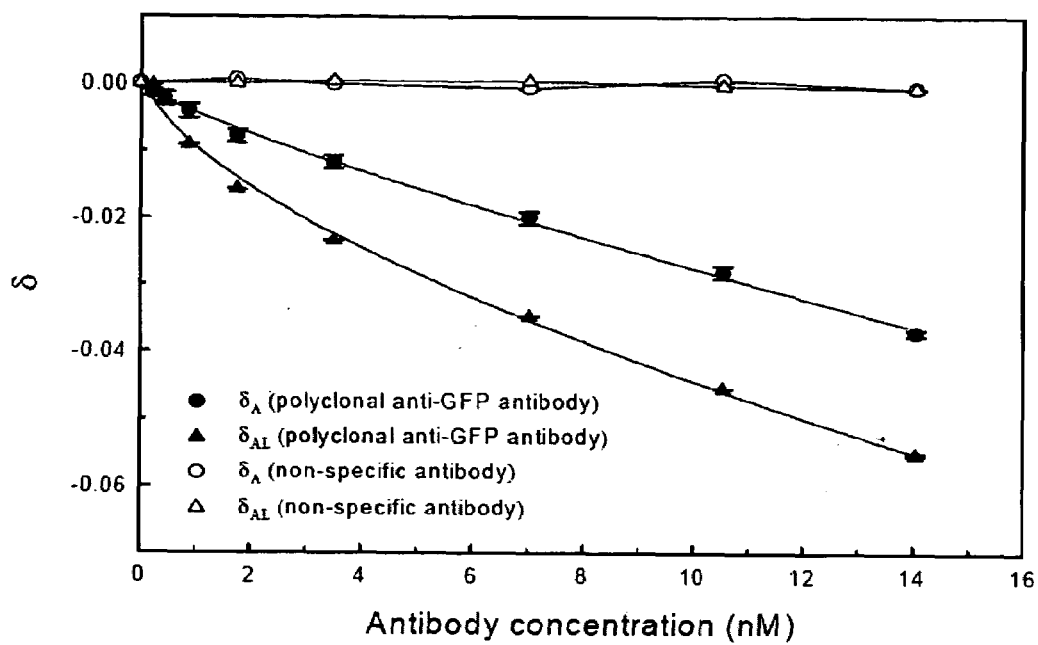

This construct exhibited an increased FRET ratio (R) in the presence of maltose due to a conformational change in the MBP portion of the molecule which results in the fluorophores coming into closer proximity to one another. Several different concentrations of the construct were incubated with anti-GFP polyclonal antibodies (which bind ECFP and EYFP), both in the presence and absence of maltose. As shown in FIGS. 7A and 7B, the FRET ratio of the sensor construct decreased in the presence of the anti-GFP antibodies, which by binding to GFP interfered with a FRET effect between the RET acceptor and RET donor of the construct. FRET emissions from this construct were further measured in the presence of antibodies not specific for GFP, resulting in virtually no change in FRET emission intensity. These results are shown in FIG. 7C, which also includes the results shown in FIG. 7B for comparison.

Figure 7D:
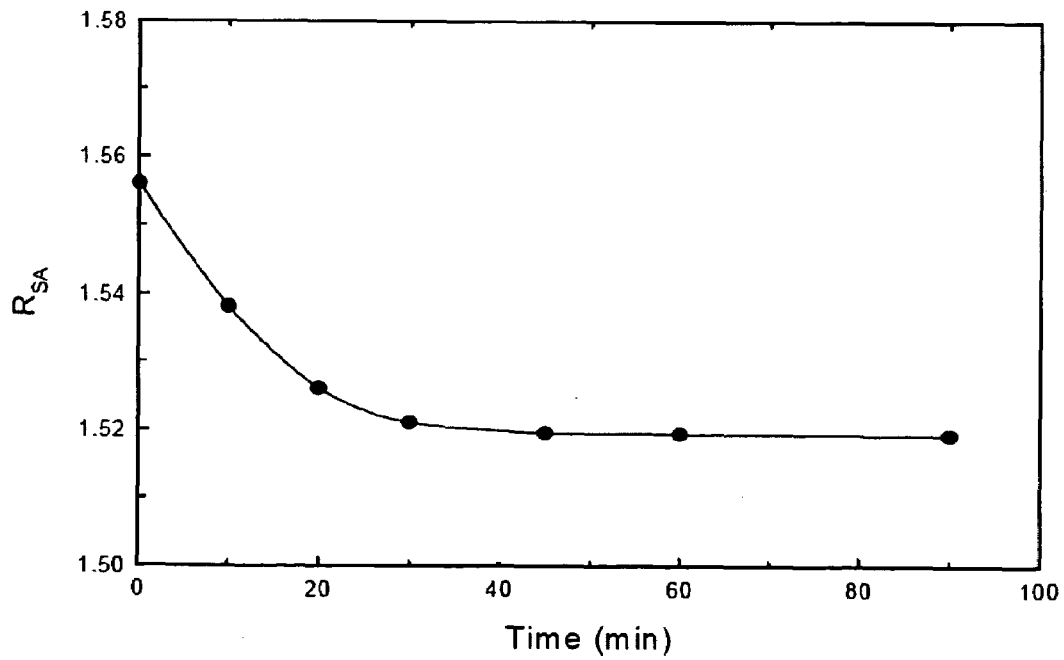
Figure 7E:
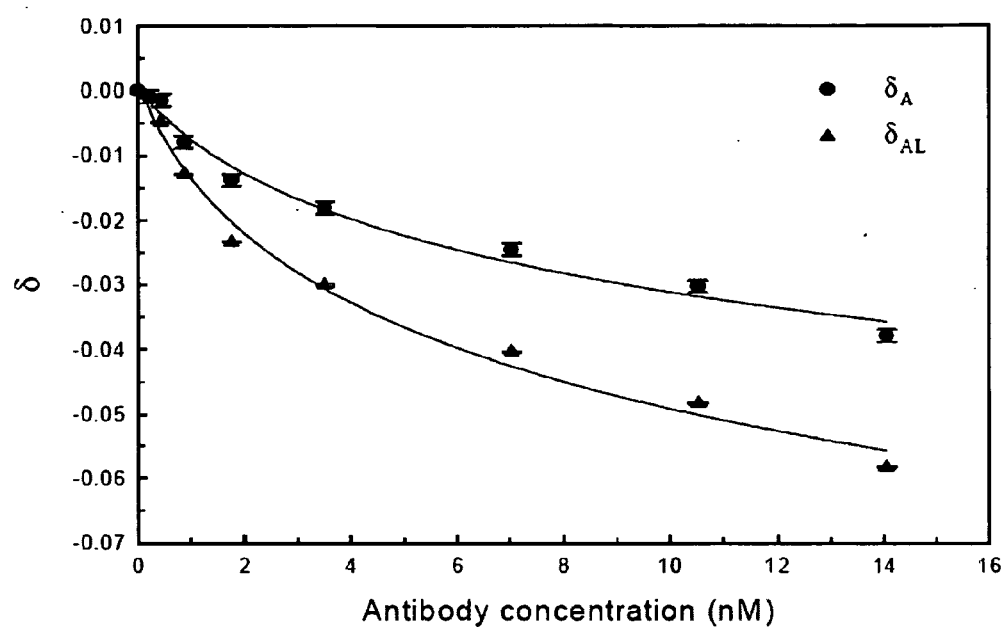
Figure 7F:
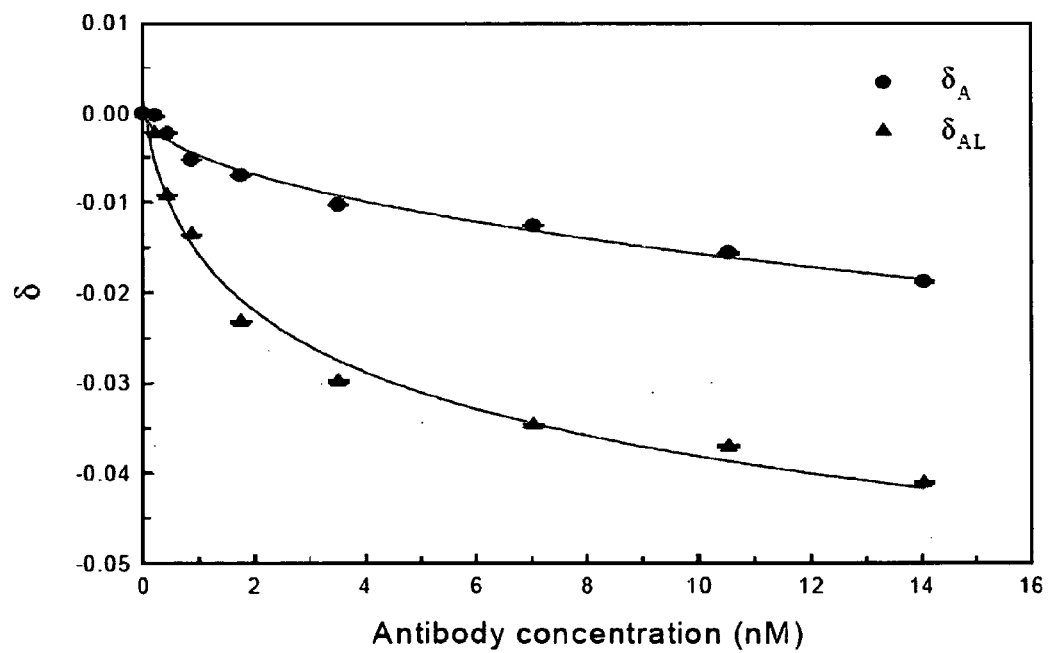
Figure 7G:
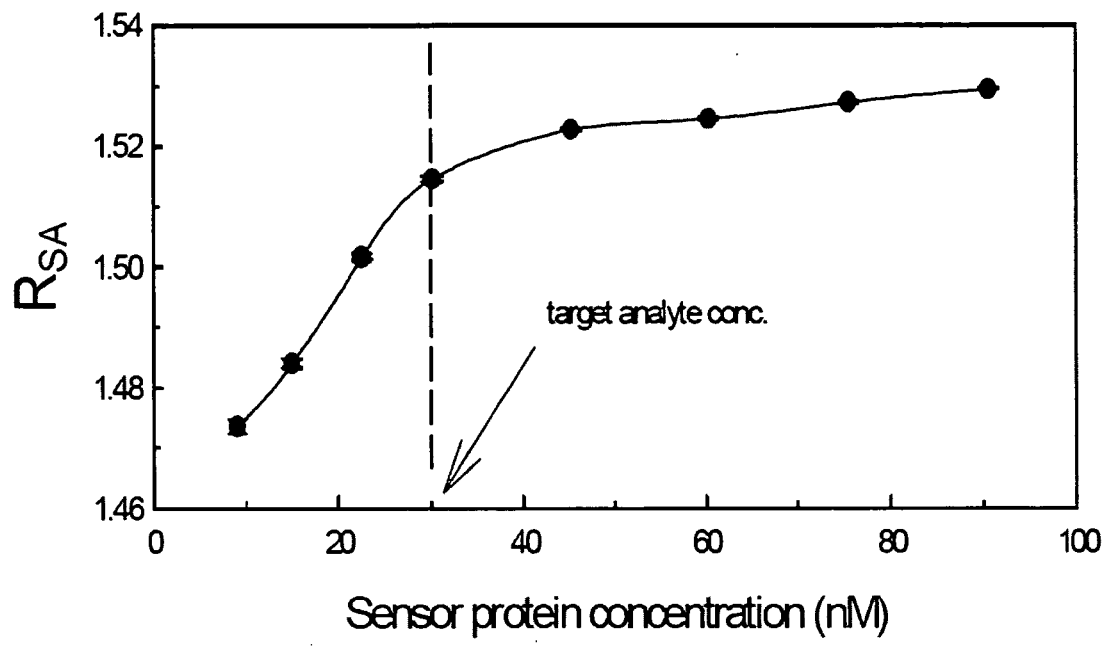
Figure 7H:
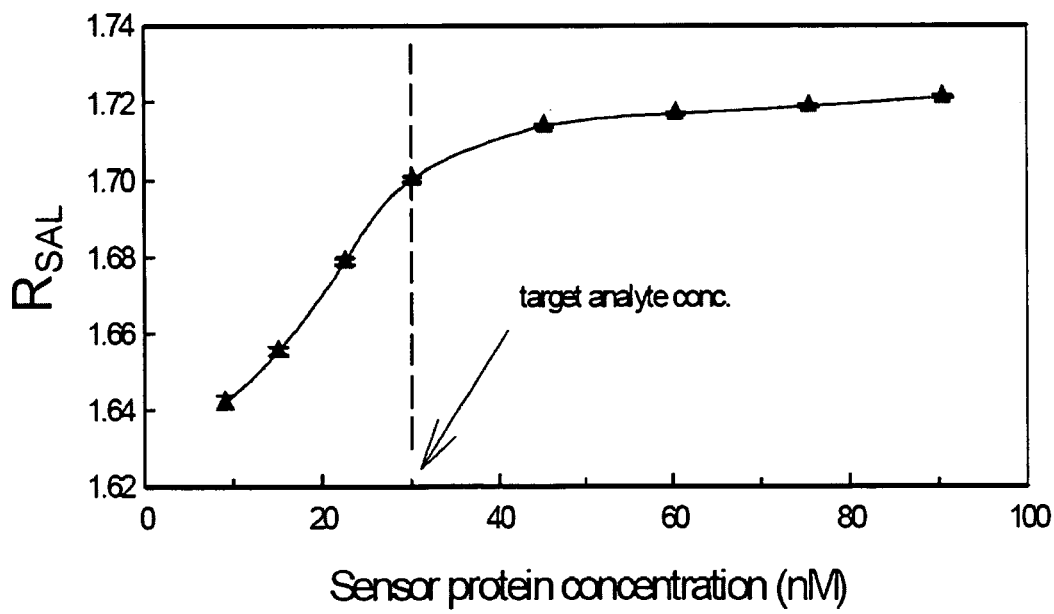
Figure 7I:
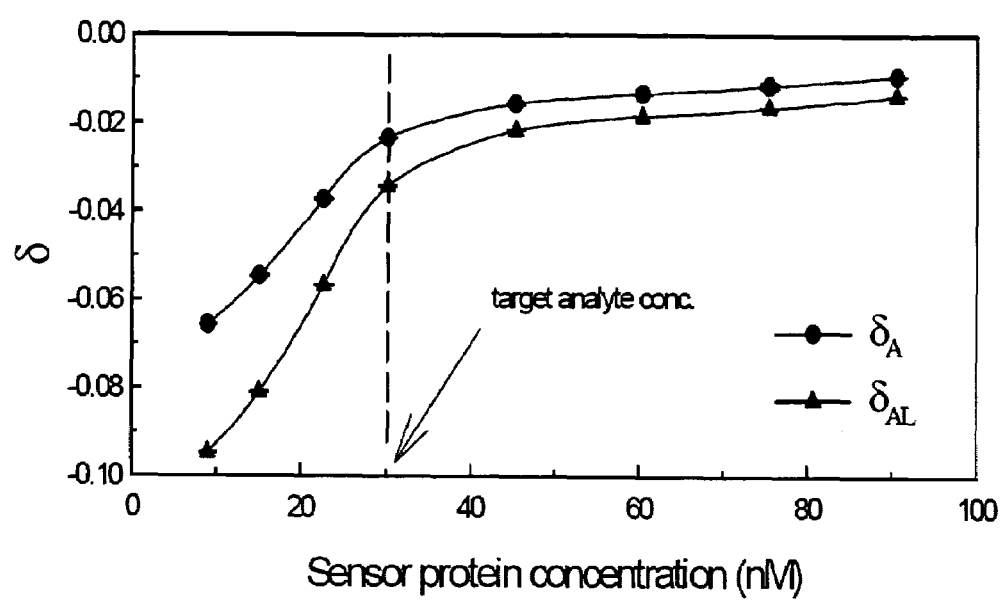

Similar trends in the FRET ratio decline from the sensor were observed with monoclonal anti-GFP antibody and a monoclonal anti-His tag antibody, as shown in FIGS. 7E and 7F, respectively. The FRET ratio of the sensor protein upon binding to the target (the anti-GFP polyclonal antibody, in this case) was further measured as a function of time. As shown in FIG. 7D, the changes in FRET ratio occurred almost right away, with a maximum decrease measured after about 30 minutes in this system. The quantitative nature of the present method was shown by testing the change in FRET ratio as a function of sensor concentration. For this experiment, a fixed concentration of polyclonal anti-GFP antibody (30 nM) was used as the target analyte and the changes in FRET ratio of the sensor were measured under varying sensor concentrations. As shown in FIG. 7G, the sensor signal (FRET ratio) begins to saturate at about 30 nM, correctly indicating the concentration of the target analyte (i.e. the polyclonal anti-GFP antibody).

Example 2

Sensor Construct Comprising MBP as the Molecular Scaffold for Detecting His-Tagged Proteins in Solution A sensor construct similar to that described in Example 1 is produced comprising a recombinant maltose binding protein having a ECFP moiety attached to its N-terminus and a EYFP moiety attached to its C-terminus. Unlike in Example 1, however, this fusion protein does not contain a hexa-histidine tag. The N terminus of ECFP or the C-terminus of EYFP is mutated to incorporate a cysteine residue which allows chemical conjugation with a thiol-reactive nitrilotriacetic acid (Maleimido-$C_3$-NTA; DoJindo, Gaithersburg, Md.). The conjugated nitrilotriacetic acid is used to chelate metal ions such as nickel which in turn binds histidine-tagged proteins. Alternatively, the nitrilotriacetic acid group can be coupled to the maltose binding protein at a location between its N- and C-terminus using site-directed mutatgenesis and chemical conjugation techniques known to the art. This sensor can be used to detect proteins which comprise a His tag.

Example 3

Self-Assembling Sensor Construct Comprising a Coiled Coil as the Molecular Scaffold for Detecting His-Tagged Proteins in Solution A sensor construct comprising heterodimeric coiled coils as the molecular scaffold is produced as follows. An E-coil (EVSALEK heptad sequence) is coupled to a WinZip-A2 coil (see, e.g., J. Mol. Biol. 2000 Jan. 21;295(3):627-39) via a peptide linker, using recombinant methods know to the art. The N-terminus of the E-coil is mutated to incorporate a cysteine residue for thiol coupling to a RET label. A K-coil (KVSALKE heptad sequence) modified with a N-terminal cysteine is produced by chemical peptide synthesis or recombinant means and labeled with a thiol-reactive nitrilotriacetic acid. In addition, an E-coil (with its N-terminus mutated to incorporate a cysteine residue for thiol coupling to a RET label) is coupled to a WinZip-B1 coil (see, e.g., J. Mol. Biol. 2000 Jan. 21;295(3):627-39) via a peptide linker, using genetic fusion and recombinant methods know to the art. These three peptide coils are incubated together and allowed to form self-assembled coiled coil sensor constructs depicted in FIG. 5A. Upon binding to a His-tagged protein, the FRET property of the sensor construct will change as depicted in FIG. 5B.

Example 4

Self-Assembling Sensor Construct Comprising Recombinant Fv Antibody

A sensor construct comprising a recombinant Fv antibody fragment is produced by separately producing two fusion proteins (see, e.g., J Mol Biol. 2001 Sep. 7;312(1):221-8). The first fusion protein comprises the VH portion of a Fv molecule linked at its C-terminus to a linker which connects it to the N-terminus of a peptide coil, WinZip-A2 to form VH::linker::WinZip-A2. The linker comprises a flexible, 14 amino acid peptide about 2.4-2.6 nm long consisting of the amino acids Gly, Ser, Thr, Pro. The second fusion protein comprises the VL portion of the Fv molecule linked at its C-terminus to a linker which connects it to the N-terminus of another peptide coil, WinZip-B1 to form VL::linker::WinZip-B1. The linker for the second fusion protein likewise comprises a flexible, 14 amino acid peptide about 2.4-2.6 nm long consisting of the amino acids Gly, Ser, Thr, Pro.

PpL and SPA-E are then used to label the two fusion proteins. Hexa-histidine tagged PpL and SPA-E are expressed in *E. coli*, purified by immobilized metal affinity chromatography (IMAC), and respectively labeled with a RET donor and a RET acceptor fluorophore. Fluorophore-labeled PpL and SPA-E are then incubated with the appropriate fusion protein to allow specific binding to the VL and VH domains, respectively.

Example 5

Self-Assembling Sensor Construct Comprising a Monoclonal Antibody

Fluorophore-conjugated PpL and SPA-E are produced as described in Example 4 for use in labeling the VH and VL regions of a monoclonal antibody. While PpL binds only the framework region of VL, SPA-E binds both to VH, and, to a lesser extent, to Fc. Since the binding affinity of SPA-E to Fc is less than that of the Fc-binding *Streptococcus* Protein-G B1 (SPG-B1) domain, the monoclonal antibodies are first incubated with SPG-B1 to block the binding of SPA-E to Fc. The fluorophore-labeled PpL and SPA-E are then incubated with the antibodies.

Although the present invention has been discussed in considerable detail with reference to certain preferred embodiments, other embodiments are possible. The steps disclosed for the present methods are not intended to be limiting nor are they intended to indicate that each step depicted is essential to the method, but instead are exemplary steps only. Therefore, the scope of the appended claims should not be limited to the description of preferred embodiments contained in this disclosure. All references cited herein are incorporated by reference to their entirety.

What is claimed is:

1. A method for determining the presence of an analyte in a sample, comprising the steps of:
    (a) providing a sensor construct comprising in a single molecule:
        (i) a molecular scaffold;
        (ii) a first label comprising an RET donor bound to the molecular scaffold;
        (iii) a second label comprising an RET acceptor bound to the molecular scaffold, wherein the RET acceptor is separated from the RET donor by a distance that allows a FRET interaction to occur between the RET donor and the RET acceptor; and
        (iv) a molecular recognition domain which specifically binds the analyte without producing a conformational change in the molecular scaffold, wherein the molecular recognition domain is bound to a component of the sensor construct selected from the group consisting of the molecular scaffold, the first label, and the second label;
    (b) contacting the sample with the sensor construct, wherein an altered FRET interaction between the RET donor and the RET acceptor occurs when the molecular recognition domain binds the analyte in the sample, thereby producing an optical signal directly in response to binding the analyte, wherein the first label, the second label, and the molecular recognition domain remain bound to the molecular scaffold as a single molecule when the molecular recognition domain binds the analyte; and
    (c) detecting the optical signal, thereby determining the presence of the analyte in the sample.

2. The method of claim 1, wherein the RET donor is selected from the group consisting of a fluorescent protein, a luminescent protein, a non-protein fluorophore, a non-protein chemiluminescent compound, and a fluorescent nanocrystal.

3. The method of claim 2, wherein the RET donor is a fluorescent protein selected from the group consisting of GFP, EGFP, RFP, BFP, CFP, ECFP, YFP, EYFP, and derivatives of one of the foregoing.

4. The method of claim 1, wherein the RET acceptor is selected from the group consisting of a fluorescent protein, a non-protein fluorophore, a fluorescent nanocrystal, and a quencher.

5. The method of claim 4, wherein the RET acceptor is a fluorescent protein selected from the group consisting of GFP, EGFP, RFP, BFP, CFP, ECFP, YFP, EYFP, and derivatives of one of the foregoing.

6. The method of claim 1, further comprising a plurality of RET donors and RET acceptors.

7. The method of claim 1, further comprising the steps of:
measuring a control optical signal produced by a FRET interaction between the RET donor and the RET acceptor prior to contacting the sensor construct with the sample; and
determining the difference between the control optical signal and the optical signal produced in step (b), wherein the difference between the control optical signal and the optical signal produced in step (b) is indicative of the amount of the analyte in the sample.

8. The method of claim 7, wherein determining the difference between the control optical signal and the optical signal produced in step (b) comprises measuring a change in the intensity of light emissions from the sensor construct.

9. The method of claim 7, wherein determining the difference between the control optical signal and the optical signal produced in step (b) comprises measuring a change in the decay kinetics of light emissions from the sensor construct.

10. The method of claim 1, wherein the molecular scaffold is bound to the RET donor with a flexible linker.

11. The method of claim 1, wherein the molecular scaffold is bound to the RET donor with a rigid linker.

12. The method of claim 1, wherein the molecular scaffold is bound to the RET acceptor with a flexible linker.

13. The method of claim 1, wherein the molecular scaffold is bound to the RET acceptor with a rigid linker.

14. The method of claim 1, wherein the molecular recognition domain comprises a polypeptide.

15. The method of claim 14, wherein a further component of the sensor construct comprises a polypeptide, the further component being selected from the group consisting of the molecular scaffold, the first label, and the second label, and wherein the molecular recognition domain is recombinantly expressed within the further component of the sensor construct, the molecular recognition domain and further component thereby comprising a recombinantly expressed fusion protein.

16. The method of claim 1, wherein the molecular recognition domain comprises a chelated metal.

17. The method of claim 1, wherein the molecular recognition domain comprises an oligonucleotide.

18. The method of claim 1, wherein the molecular scaffold of the sensor construct comprises a polypeptide.

19. The method of claim 18, wherein the polypeptide comprises an antibody.

20. The method of claim 19, wherein the first label comprises the E domain of Protein A and the second label comprises a binding domain of Protein L.

21. The method of claim 18, wherein the polypeptide comprises a single-chain Fv, and wherein the molecular recognition domain comprises a CDR region of the single-chain Fv.

22. The method of claim 18, wherein the polypeptide comprises an Fv portion of an antibody, and the molecular recognition domain comprises a CDR region of the Fv portion.

23. The method of claim 18, wherein the polypeptide is derived from a periplasmic binding protein.

24. The method of claim 18, wherein the first label is a fluorescent protein produced together with the molecular scaffold as a single polypeptide molecule.

25. The method of claim 18, wherein the first label and the molecular scaffold are joined by chemical ligation.

26. The method of claim 18, wherein the second label is a fluorescent protein produced together with the molecular scaffold as a single polypeptide molecule.

27. The method of claim 18, wherein the second label and the molecular scaffold are joined by chemical ligation.

28. The method of claim 18, wherein the molecular recognition domain is chemically coupled to a component of the sensor construct selected from the group consisting of the molecular scaffold, the first label, and the second label.

29. The method of claim 18, wherein the molecular scaffold comprises a pair of heterodimeric coiled coil polypeptides.

30. The method of claim 29, wherein the pair of heterodimeric coiled coil polypeptides is selected from the group consisting of a WinZip-A2/WinZip-B1 coil pair and an E/K coil pair.

31. The method of claim 1, wherein the first label comprises a plurality of RET donors.

32. The method of claim 1, wherein the second label comprises a plurality of RET acceptors.

33. The method of claim 1, wherein the molecular recognition domain of the sensor construct provided in step (a) is bound to the molecular scaffold of the sensor construct.

34. The method of claim 1, wherein the molecular recognition domain of the sensor construct provided in step (a) is bound to a component of the sensor construct selected from the group consisting of the first label and the second label.

* * * * *